(12) United States Patent
Chin et al.

(10) Patent No.: US 8,497,231 B2
(45) Date of Patent: Jul. 30, 2013

(54) EVOLVED ORTHOGONAL RIBOSOMES

(75) Inventors: Jason Chin, Cambridge (GB); Kaihang Wang, Cambridge (GB); Heinz Neumann, Cambridge (GB)

(73) Assignee: Medical Research Council, London (GB)

( * ) Notice: Subject to any disclaimer, the term of this patent is extended or adjusted under 35 U.S.C. 154(b) by 109 days.

(21) Appl. No.: 12/516,230

(22) PCT Filed: Nov. 28, 2007

(86) PCT No.: PCT/GB2007/004562
§ 371 (c)(1),
(2), (4) Date: Dec. 15, 2009

(87) PCT Pub. No.: WO2008/065398
PCT Pub. Date: Jun. 5, 2008

(65) Prior Publication Data
US 2010/0105565 A1   Apr. 29, 2010

Related U.S. Application Data

(60) Provisional application No. 60/939,906, filed on May 24, 2007.

(30) Foreign Application Priority Data

Nov. 30, 2006  (GB) .................................. 0623974.3
May 25, 2007  (GB) .................................. 0710094.4

(51) Int. Cl.
*C40B 50/06*  (2006.01)
*C07H 21/02*  (2006.01)
*A61K 38/00*  (2006.01)
*C07K 4/00*  (2006.01)

(52) U.S. Cl.
USPC ............................ 506/26; 536/23.1; 530/300

(58) Field of Classification Search
None
See application file for complete search history.

(56) References Cited

FOREIGN PATENT DOCUMENTS
WO   2004/035743    4/2004
WO   07/10221       1/2007

OTHER PUBLICATIONS

Brosius et al, Complete nucleotide sequence of a 16S ribosomal RNA gene from *Escherichia coli*, Proc. Natl. Acad. Sci. USA vol. 75, No. 10, pp. 4801-4805, Oct. 1978, Biochemistry.*
Gesteland et al., Recoding: Dynamic Reprogramming of Translation, Annu. Rev. Biochem. (1996) 65:741-68.*
Adleman et al., Science, 266:1021-1024 (1994).
Anderson et al., Chem. Biol., 9:237-244 (2002).
Arkov et al., EMBO J., 27:1507-1514 (1998).
Atkins et al., Annu. Rev. Genet., 25:201-228 (1991).

(Continued)

*Primary Examiner* — James Ketter
*Assistant Examiner* — Reza Ghafoorian
(74) *Attorney, Agent, or Firm* — McAndrews Held & Malloy, Ltd.

(57) ABSTRACT

There is provided a method for evolving an orthogonal rRNA molecule, comprising the steps of: providing one or more libraries of mutant orthogonal rRNA molecules and introducing the libraries into cells such that the orthogonal rRNA is incorporated into ribosomes to provide orthogonal ribosomes; providing one or more orthogonal mRNA molecules which (i) are not translated by natural ribosomes, and (ii) comprise one or more orthogonal mRNA codons; assaying the translation of the orthogonal mRNA and selecting the orthogonal rRNA molecules which translate the orthogonal mRNA, wherein the assay in step (c) requires translation of one or more orthogonal mRNA codons in the orthogonal mRNA; and orthogonal ribosomes incorporating such rRNA molecules.

6 Claims, 16 Drawing Sheets

OTHER PUBLICATIONS

Atkins et al., Cold Spring Harb. Symp. Quant. Biol., 66:217-232 (2001).
Bain et al., J. Am. Chem. Soc., 111:8013-8014 (1989).
Benenson et al., Nature, 414:430-434 (2001).
Blattner et al., Science, 277:1453-1462 (1997).
Bossi et al., Cell, 25:489-496 (1981).
Bossi et al., J. Mol. Biol., 164:73-87 (1983).
Carter et al., Nature, 407:340-348 (2000).
Caskey et al., Science, 162:135-138 (1968).
Chin et al., ChemBioChem., 3:1135-1137 (2002).
Chin et al., Science, 301:964-967 (2003).
Crick, J. Mol. Biol., 19:548-555 (1966).
Crick, Nature, 192:1227-1232 (1961).
Curran et al., Science, 238:1545-1550 (1987).
Datta et al., Microbiologica, 8:73-77 (1985).
Dougherty, Curr. Opin. Chem. Biol., 4:645-652 (2000).
England et al., Cell, 96:89-98 (1999).
Heckler et al., Biochemistry, 23:1468-1473 (1984).
Janzen et al., Cold Spring Harb. Symp. Quant. Biol., 66:459-467 (2001).
Kleina et al., J. Mol. Biol., 213:705-717 (1990).
Kohrer et al., Chem. Biol., 10:1095-1102 (2003).
Korostelev et al., Cell, 126:1065-1077 (2006).
Liebhaber et al., J. Mol. Biol., 226:609-621 (1992).
Link et al., Curr. Opin. Biotechnol., 14:603-609 (2003).
Ludwig et al., FEMS Microbiol. Rev., 15:155-173 (1994).
Lummis et al., Nature, 438:248-252 (2005).
Mori et al., Proc. Natl. Acad. Sci. USA, (2006).
Noren et al., Science, 244:182-188 (1989).
Nowak et al., Methods Enzymol., 293:504-529 (1998).
Nowak et al., Science, 268:439-442 (1995).
Ogle et al., Trends Biochem. Sci., 28:259-266 (2003).
Ohtsuki et al., FEBS Lett., 579:6769-6774 (2005).
Petry et al., Cell, 123:1255-1266 (2005).
Rackham et al., J. Am. Chem. Soc., 127:17584-17585 (2005).
Ramakrishnan, Cell, 108:557-572 (2002).
Riddle et al., Nat. New Biol., 242:230-234 (1973).
Riyasaty et al., J. Mol. Biol., 34:541-557 (1968).
Roth, Cell, 24:601-602 (1981).
Ryu et al., Nat. Methods, 3:263-265 (2006).
Schlieker et al., Nat. Struct. Mol. Biol., 11:607-615 (2004).
Schuwirth et al., Science, 310:827-834 (2005).
Selmer et al., Science, 313:1935-1942 (2006).
Short et al., Biochemistry, 38:8808-8819 (1999).
Shultzaberger et al., J. Mol. Biol., 313:215-228 (2001).
Sisido et al., Methods, 36:270-278 (2005).
Stadtman, Annu. Rev. Biochem., 65:83-100 (1996).
Stahl et al., Trends Biochem. Sci., 27:178-183 (2002).
Taira et al., J. Biosci. Bioeng., 99:473-476 (2005).
Taki et al., ChemBioChem, 7:425-428 (2006).
Tatusova et al., FEMS Microbiol. Lett., 174:247-250 (1999).
Tuohy et al., J. Mol. Biol., 228:1042-1054 (1992).
Wang et al., Science, 292:498-500 (2001).
Weibezahn et al., Cell, 119:653-665 (2004).
Wikstrom et al., J. Mol. Biol., 224:949-966 (1992).
Winkler et al., Nature, 419:952-956 (2002).
Wood et al., Biotechnol. Bioeng., 38:891-906 (1991).
Youngman et al., Cold Spring Harb. Symp. Quant. Biol., 71:545-549 (2006).
Yusupova et al., Cell, 106:233-241 (2001).
Zhang et al., J. Mol. Biol., 242:614-618 (1994).
Anderson et al., Proc. Natl. Acad. Sci. USA, 101:7566-7571 (2004).
Cannone et al., BMC Bioinformatics, 3:2 (2002).
Capecchi, Proc. Natl. Acad. Sci. USA, 58:1144-1151 (1967).
Chen et al., Nucleic Acids Res., 22:4953-4957 (1994).
Chin et al., Proc. Natl. Acad. Sci. USA, 99:11020-11024 (2002).
Cole et al., Nucleic Acids Res., 33(Database issue):D294-D296 (2005).
Dunny et al., Appl. Environ. Microbiol., 57:1194-1201 (1991).
Furter, Protein Sci., 7:419-426 (1998).
Hansen et al., EMBO Resp., 4:499-504 (2003).
Hui et al., Proc. Natl. Acad. Sci. USA, 84:4762-4766 (1987).
International Search Report in PCT/GB07/04562, dated Jun. 3, 2008.
Jacob et al., Proc. Natl. Acad. Sci. USA, 84:4757-4761 (1987).
Kauer et al., J. Biol. Chem., 261:10695-10700 (1986).
Kohrer et al., Proc. Natl. Acad. Sci. USA, 98:14310-14315 (2001).
Kramer et al., RNA, 13:87-96 (2007).
Laursen et al., Microbiol. Mol. Biol. Rev., 69:101-123 (2005).
Looman et al., Nucleic Acids Res., 14:5481-5497 (1986).
Lutz et al., Nucleic Acids Res., 25:1203-1210 (1997).
Moore et al., Nucleic Acids Res., 28:3615-3624 (2000).
Murakami et al., Nucleic Acids Symp. Ser. (Oxf.), (50):35-36 (2006).
Murray et al., Antimicrob. Agents Chemother., 41:1-6 (1997).
O'Connor et al., Nucleic Acids Res., 25:1185-1193 (1997).
Prescott et al., Nucleic Acids Res., 20:1567-1571 (1992).
Rackham et al., Nat. Chem. Biol., 1:159-166 (2005).
Rice et al., J. Biol. Chem., 259:6505-6510 (1984).
Rodriguez et al., Proc. Natl. Acad. Sci. USA, 103:8650-8655 (2006).
Sakamoto et al., Nucleic Acids Res., 30:4692-4699 (2002).
Scolnick et al., Proc. Natl. Acad. Sci. USA, 61:768-774 (1968).
Shine et al., Biochem. J., 141:609-615 (1974).
Sprinzl et al., Nucleic Acids Res., 26:148-153 (1998).
Steer et al., J. Biol. Chem., 274:35601-35606 (1999).
Steitz et al., Proc. Natl. Acad. Sci. USA, 72:4734-4738 (1975).
Triman et al., Nucleic Acids Res., 26:280-284 (1998).
Wang et al., Nat. Biotechnol., 25:770-777 (2007).
Xie et al., Nat. Rev. Mol. Cell Biol., 7:775-782 (2006).
Olejniczak et al., Nat. Struct. Mol. Biol., 12:788-793 (2005).
Gesteland et al., Annu. Rev. Biochem., 65:741-786 (1996).
Hino et al., Nat. Methods, 2:201-206 (2005).
Hohsaka et al., J. Am. Chem. Soc., 118:9778-9779 (1996).

* cited by examiner

```
        G—C                 G—C                 G—C                 G—C
        G—C                 G—C                 G—C                 G—C
        C—G                 C—G                 C—G                 C—G
        C—G                 C—G                 C—G                 C—G
        A—U                 A—U                 A—U                 A—U
    38C      A 32        38C      A 32       38C      A 32       38C      A 32
    A        U            A        U          A        U          A        U
     A  U  C  U 33.5       A  U  C  C 33.5     A  U  C  G 33.5     A  U  C  A 33.5
     |  |  |  |            |  |  |  |          |  |  |  |          |  |  |  |
   5'-U  A  G  A-3'       5'-U A  G  G-3'    5'-U A  G  C-3'     5'-U A  G  U-3'
```

| | | | |
|---|---|---|---|
| O-ribosome | 25 | 15 | 10 | 10 |
| Ribo-X | 125 | 120 | 40 | 15 |
| Enhancement | 5 | 6 | 4 | 1.5 |

```
        G—C                 G—C                 G—C                 G—C
        G—C                 G—C                 G—C                 G—C
        C—G                 C—G                 C—G                 C—G
        C—G                 C—G                 C—G                 C—G
        A—U                 A—U                 A—U                 A—U
   38A       G32         38C      A 32       38A      C32        38C      A 32
    U        U            A        U          A        U          A        U
     G  G  G  A 33.5       U  C  C  U 33.5     U  C  C  U 33.5     A  U  C
     |  |  |  |            |  |  |  |          |  |  |  |          |  |  |
   5'-C  C  C  U-3'      5'-A G  G  A-3'    5'-A G  G  A-3'     5'-U A  G-3'
```

| | | | |
|---|---|---|---|
| O-ribosome | 10 | 80 | 80 | 15 |
| Ribo-X | 25 | 140 | 80 | 100 |
| Enhancement | 2.5 | 1.7 | 1 | 8 |

FIG. 4

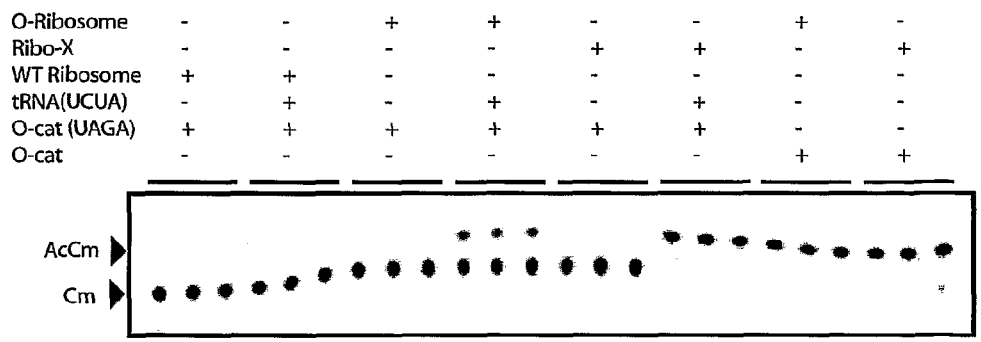
FIG. 5
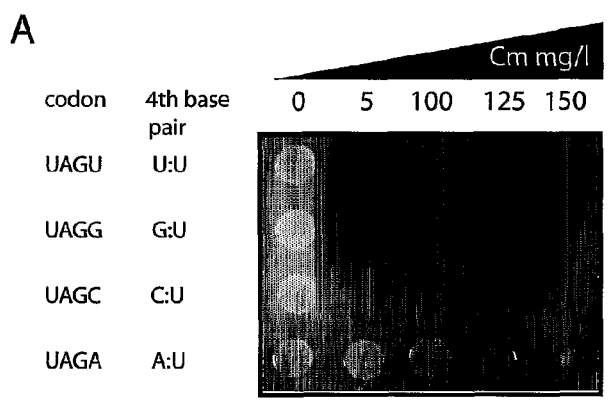
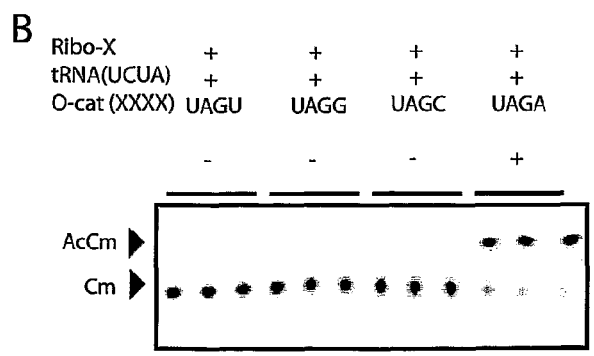
FIG. 6

Supplementary Table 1| 528/36 16S rDNA Libraries Construction

| | Randomized Nucleotide | Combinations $4^N$ | No. of clones for 99% coverage | Actual Library Size |
|---|---|---|---|---|
| N5 | 5 | $4^5 = 1,024$ | 4,716 | $2.4 \times 10^7$ |
| N6 | 6 | $4^6 = 4,096$ | 18,862 | $3.6 \times 10^7$ |
| N7 | 7 | $4^7 = 16,384$ | 75,448 | $1.0 \times 10^5$ |
| N8 | 8 | $4^8 = 65,636$ | 301,793 | $5.0 \times 10^7$ |
| N9 | 9 | $4^9 = 262,144$ | 1,207,173 | $4.2 \times 10^7$ |

FIG. 12

Supplementary Table 2| Primers Used

| Name | Sequence (5' – 3') | Purpose |
|---|---|---|
| 528/36N5f wd | GGAAAGGTCTCAGCAGCCGCNNNNNCGGAGGGT GCAAGCGTTAATCGGAATTAC (SEQ ID NO:35) | 528/36N5 library construction |
| 528/36N6f wd | GGAAAGGTCTCAGCAGCCGCNNNNNNCGGAGG TGCAAGCGTTAATCGGAATTAC (SEQ ID NO:36) | 528/36N6 library construction |
| 528/36N7f wd | GGAAAGGTCTCAGCAGCCGCNNNNNNNCGGAGG GTGCAAGCGTTAATCGGAATTAC (SEQ ID NO:37) | 528/36N7 library construction |
| 528/36N8f wd | GGAAAGGTCTCAGCAGCCGCNNNNNNNNCGGAG GGTGCAAGCGTTAATCGGAATTAC (SEQ ID NO:38) | 528/36N8 library construction |
| 528/36N9f wd | GGAAAGGTCTCAGCAGCCGCNNNNNNNNNCGGA GGGTGCAAGCGTTAATCGGAATTAC (SEQ ID NO:39) | 528/36N9 library construction |
| 528/36revL | GAGTAGGTCTCACTGCTGGCACGGAGTTAGCCGG TGCTTCTTCTG (SEQ ID NO:40) | 528/36N5,6,7,8,9 libraries construction |
| 1fSer2Fla | CACAAGTATACGCCGCTTCTTTGAGCGAACGATC AAAAATAAGTGGCGCCCATCAAAAAAATATTCT CAACATAAAAAACTTTGTGTAATACTTG (SEQ ID NO:41) | Ser$^2$ tRNA with mutated ASL, primer assembly |
| 2fSer2Fla | CTCAACATAAAAAACTTTGTGTAATACTTGTAACG CTGAATTCACGTGGCCGGCCATATGGGAGAGATG CCGGAGCGGCTGAACGGAC (SEQ ID NO:42) | Ser$^2$ tRNA with mutated ASL, primer assembly |
| 3rSer2Fla | GTGGCGGAGAGAGGGGGATTTGAACCCCCGGTAG AGTTGCCCCTACTCCGGTGTTAGAATACCGGTCCG TTCAGCCGCTCCGGCATCTCTC (SEQ ID NO:43) | Ser$^2$ tRNA with mutated ASL, primer assembly |
| 4rSer2Fla | CACAAGTATACTTAAAAAAAATCCTTAGCTTTCGC TAAGGATCTGCAGCCCGGGCGCGCCTAGGTGGCG GAGAGAGGGGGATTTGAAC (SEQ ID NO:44) | Ser$^2$ tRNA with mutated ASL, primer assembly |
| CATS103T AGAfw | CAGACTGAAACGTTTTAGATCGCTCTGGAGTGAA TACCACGACGATTTCC (SEQ ID NO:45) | TAGA mutation at Ser 103 |
| CATS103T AGArv | TTCACTCCAGAGCGATCTAAAACGTTTCAGTCTGC TCATGGAAAACGGTG (SEQ ID NO:46) | TAGA mutation at Ser 103 |
| CATS146T AGAfw | AATATGTTTTTCGTCTAGAGCCAATCCCTGGGTGA GTTTCACCAGTTTTG (SEQ ID NO:47) | TAGA mutation at Ser 146 |
| CATS146T | CACCCAGGGATTGGCTCTAGACGAAAAACATATT | TAGA mutation at |

FIG. 13

| | | |
|---|---|---|
| AGArv | CTCAATAAACCCTTTAG (SEQ ID NO:48) | Ser 146 |
| CATS103T AGfw | CAGACTGAAACGTTTTAGTCGCTCTGGAGTGAAT ACCACGACGATTTCC (SEQ ID NO:49) | TAG mutation at Ser 103 |
| CATS103T AGrv | TTCACTCCAGAGCGACTAAAACGTTTCAGTCTGCT CATGGAAAACGGTG (SEQ ID NO:50) | TAG mutation at Ser 103 |
| CATS146T AGfw | AATATGTTTTTCGTCTAGGCCAATCCCTGGGTGAG TTTCACCAGTTTTG (SEQ ID NO:51) | TAG mutation at Ser 146 |
| CATS146T AGrv | CACCCAGGGATTGGCCTAGACGAAAAACATATTC TCAATAAACCCTTTAG (SEQ ID NO:52) | TAG mutation at Ser 146 |
| TRNAtagtf w | CTACTCCGGTGTTAGTATACCGGTCCGTTCAGCCG CTCCGGCATCTCTCC (SEQ ID NO:53) | anti-UAGA $Ser^2$ tRNA with mutated ASL |
| TRNAtagtr v | TGAACGGACCGGTATACTAACACCGGAGTAGGGG CAACTCTACCGGGGGT (SEQ ID NO:54) | anti-UAGA $Ser^2$ tRNA with mutated ASL |

FIG. 13 CONT'D

```
                    301              315
                    |                |
O-cat               acg ttt tca tcg ctc
aa 101-105          Thr Phe Ser Ser Leu UAGA103             acg ttt uaga tcg ctc
                    Thr Phe Quad Ser Leu UAG103              acg ttt uag agt ctc
                    Thr Phe Amb Ser Leu 430              444
                    |                |
O-cat               ttc gtc tca gcc aat
aa 144-148          Phe Val Ser Ala Asn UAGA146             ttc gtc uaga gcc aat
                    Phe Val Quad Ala Asn
```

```
         gst                           Linker              malE
ctg gtt ccg cgt gga tcc ccg gga att cat cgt gac ggg TAC ctc aaa atc GAA gaa ggt aaa ctg gta atc
 L   V   P   R   G   S   P   G   I   H   R   D   G   Y   L   K   I   E   E   G   K   L   V   I
                                                        UAG         UAG
     Thrombin
```

EVOLVED ORTHOGONAL RIBOSOMES

The present application is filed pursuant to 35 U.S.C. 371 as a U.S. National Phase application of International Patent Application No. PCT/GB07/04562, which was filed Nov. 28, 2007, claiming the benefit of priority to British Patent Application No. 0623974.3, which was filed on Nov. 30, 2006, U.S. Patent Application No. 60/939,906, which was filed on May 24, 2007, and British Patent Application No. 0710094.4, which was filed on May 25, 2007. The entire text of the aforementioned. PCT/GB07/04562 is incorporated herein by reference in its entirety.

The present invention relates to orthogonal ribosomes with enhanced translation efficiency for orthogonal RNA. In particular, the invention provides orthogonal ribosomes with enhanced translation efficiency for quadruplet and amber codons.

INTRODUCTION

We recently created orthogonal ribosome-mRNA pairs that operate in parallel with, but independent of, the cellular ribosome[22]. The orthogonal mRNA contains a ribosome-binding site that does not direct translation by endogenous ribosomes but is efficiently translated by an orthogonal ribosome, which does not appreciably translate cellular mRNAs. In previous work we have explored the use of orthogonal ribosomes to create new modes of system-level translational regulation[22, 23], and to understand the relationship between ribosome structure and function[24].

The triplet nature of the genetic code[1] is conserved across all known organisms. Rare exceptions to the correspondence between an mRNA triplet sequence and the amino acid encoded include frame shifts (+1, +2, −1, −2), hops, and read-through of stop signals[2, 3]. While many programmed changes of reading frame require upstream sequences in the mRNA that recruit additional translation factors or that interact with and prepare the translational machinery for a change of reading frame, +1 frame shift mutations that create quadruplet codons can be read, independent of upstream signals, by tRNAs with extended anticodon loops[4-9]. The apparent simplicity and uniqueness of quadruplet codons as amino acid insertion signals has led to the use of extended anticodon tRNAs to encode the incorporation of unnatural amino acids, albeit with low efficiency, both in vitro[10-13] and in vivo[12, 14, 15].

The mechanism of quadruplet decoding, the efficiency of quadruplet decoding, and the range of quadruplet codon/anticodon pairs accessible to the natural translational machinery have been investigated for over 35 years[4-6, 16-19]. Recently, Schultz and coworkers explored the scope of quadruplet codon-anticodon pairs that operate with the natural translational machinery by crossing a library of extended anticodon tRNA mutants, derived from tRNAser2, with a library of quadruplet codons[8]. They discovered a group of extended anticodon tRNAs able to read their cognate quadruplet codons, including UAGA, AGGA and CCCU, in vivo. The in vivo efficiency of quadruplet decoding by extended anticodon tRNAs is poor (from less than 1% to about 20%)[6]. It is clear that the efficiency of decoding quadruplet codons with extended anticodon tRNAs is limited by the natural ribosome, that has evolved to read a triplet code.

Evolving and engineering the natural ribosome is a challenge on several levels. First, the ribosome is massive: at 2.5 MDa and containing three large RNAs and 52 proteins, it is an order of magnitude larger than most macromolecules that have been engineered or evolved. Fortunately, structural biology, biochemistry and mutagenesis have begun to provide insights into the molecular basis of ribosome function[20], and provide a molecular basis for targeted efforts to expand ribosome function. Second, the ribosome is essential, and highly conserved. Many mutations in ribosomal components are dominant negative, deleterious or lethal since they compromise the efficient and accurate synthesis of the proteome[21].

The genetic code of prokaryotic and eukaryotic organisms has been expanded to allow the in vivo, site-specific incorporation of over 20 designer unnatural amino acids in response to the amber stop codon. This synthetic genetic code expansion is accomplished by endowing organisms with evolved orthogonal aminoacyl-tRNA synthetase/tRNA$_{CUA}$ pairs that direct the site-specific incorporation of an unnatural amino acid in response to an amber codon. The orthogonal aminoacyl-tRNA synthetase aminoacylates a cognate orthogonal tRNA, but no other cellular tRNAs, with an unnatural amino acid, and the orthogonal tRNA is a substrate for the orthogonal synthetase but is not substantially aminoacylated by any endogenous aminoacyl-tRNA synthetase. Genetic code expansion in E. coli using evolved variants of the orthogonal Methanococcus jannaschii tyrosyl-tRNA synthetase/tRNA$_{CUA}$ pair greatly increases unnatural amino acid-containing protein yield since, in contrast to methods that rely on the addition of stoichiometrically pre-aminoacylated suppressor tRNAs to cells or to in vitro translation reactions, the orthogonal tRNA$_{CUA}$ is catalytically re-acylated by its cognate aminoacyl-tRNA synthetase enzyme, thus aminoacylation need not limit translational efficiency.

While in vivo genetic code expansion is clearly a major advance, the efficiency of site-specific unnatural amino acid incorporation in E. coli via amber suppression is severely limited; Release factor-1 (RF-1) mediated peptide chain termination competes with tRNACUA mediated chain elongation, and therefore 70-80% of polypeptide synthesis initiated on genes containing a single amber stop codon is terminated at that codon. This clearly limits (to ~20-30%) the efficiency with which proteins containing unnatural amino acids are synthesized from genes containing a single internal amber stop codon. Moreover, the efficiency of unnatural amino acid incorporation decreases drastically with increasing amber stop codons in a gene, such that less than one-tenth of protein synthesis initiated on a gene containing two amber codons typically reaches completion.

Many potential applications of unnatural amino acid mutagenesis, including the translational incorporation of amino acids corresponding to post-translational modifications present at multiple sites in proteins (eg: methylation, acetylation, phosphorylation), require more efficient methods of incorporation to make useful amounts of protein. Moreover the introduction of biophysical probes and chemically precise perturbations into proteins in their native cellular context offers the exciting possibility of understanding and controlling cellular functions in ways not previously possible. However, the large amount of truncated protein produced in these experiments may provide a substantial perturbation to precisely the system under study, confounding meaningful conclusions about the function of full-length unnatural amino acid-containing protein in the cell.

Unnatural amino acid incorporation in in vitro translation reactions can be increased by using S30 extracts containing a thermally inactivated mutant of RF-1. Unfortunately, though temperature sensitive mutants of RF-1 allow transient increases in global amber suppression in vivo, RF-1 knockouts are lethal, and are therefore not a viable option for stably and specifically increasing the efficiency of unnatural amino acid incorporation in E. coli. Increases in tRNACUA gene copy number and a transition from minimal to rich media have provided some improvement in the yield of proteins incorporating an unnatural amino acid in E. coli, but the efficiency of unnatural amino acid incorporation (defined as the ratio of full length protein to truncated protein) is still only 20-30%. Additional improvements possible through a further increase in tRNA copy number are problematic for several reasons. First, this strategy increases the extent to which natural aminoacyl-tRNA synthetases aminoacylate the orthogonal tRNA, potentially leading to natural amino acid incorporation in response to the amber, codon. Second, the plasmid encoded tRNACUA gene repeats typically used to achieve increases in tRNA copy number are prone to recombination-mediated inactivation. Third, the strategy indiscriminately increases suppression of all amber codons in the cell and therefore enhances the read-through of stop codons on chromosomal genes (320 genes in E. coli terminate in UAG, including 44 essential genes); this strategy will therefore interfere with cellular protein synthesis and potentially disturb cellular physiology.

Despite these disadvantages, we have successfully developed an orthogonal ribosome which reads orthogonal mRNA codons with enhanced efficiency compared to natural ribosomes.

SUMMARY OF THE INVENTION

Unlike the progenitor ribosome in natural cells, orthogonal ribosomes are not responsible for synthesizing the proteome, and it is therefore be possible to further diverge their function. However, this possibility had not been realised in the prior art. We have now demonstrated the first example of synthetic evolution of ribosome function in living cells. We have shown that orthogonal ribosomes can be evolved to decode more efficiently a range of extended codons using tRNAs with extended anticodon loops. The evolved orthogonal ribosome, ribo-X, preferentially reads quadruplet codons with extended anticodon tRNAs and can show specificity for Watson-Crick base pairs at the fourth position of the codon-anticodon interaction. Ribo-X also improves amber suppression by amber suppressor tRNAs. Finally we have provided experimental support for a model which explains the mode of action of ribo-X, and implicates the 530 loop, in the ribosome decoding centre, in functional interactions with RF1.

In a first aspect of the present invention, therefore, there is provided an evolved orthogonal ribosomal RNA which possesses an enhanced efficiency of tRNA-dependent reading of orthogonal mRNA codons.

The rRNA of the invention differs from orthogonal rRNA (O-rRNA) molecules of the prior art, in that it not only shows specificity for orthogonal mRNA (O-mRNA), it shows an improved efficiency of translation of orthogonal mRNA codons compared to known orthogonal or natural ribosomes.

As noted above, although the prior art does document the reading of quadruplet codons by natural ribosomes, the efficiency of such reading is at most 20% of the efficiency with which triplet codons are read. In contrast, evolved O-ribosomes according to the invention are able to decode O-codons, such as quadruplet codons, approximately 10 times more efficiently than the same O-ribosomes can decode natural triplet codons. Moreover, they are more efficient at decoding quadruplet codons than non-evolved natural or O-ribosomes.

An orthogonal RNA codon, as used herein, is a codon which does not encode one of the 20 natural amino acids in the natural genetic code. Unnatural amino acids have been incorporated into proteins using modified tRNA which is charged with a unnatural amino acid, in place of the natural tRNA; however, this has previously been achieved using natural codons, both changing their specificity though modification of tRNA. By evolving a ribosome to decode orthogonal codons, such as extended codons, more efficiently, we have taken a different approach and developed an artificial alternative to the natural genetic code. Moreover, we have improved the efficiency of incorporation of amino acids into polypeptides using orthogonal tRNA, improving the efficiency of production of proteins incorporating natural and/or non-natural amino acids using mRNA with an artificial genetic code.

Increased efficiency can be measured, for example, by comparing the relative concentrations of an antibiotic to which resistance is conferred by an O-mRNA encoding an antibiotic resistance gene. For example, an evolved O-ribosome according to the invention is able to confer resistance to chloramphenicol acetyltransferase at a concentration 10 times higher when translating a mRNA comprising an orthogonal codon than when translating a mRNA comprising only triplet codons.

Preferably, the orthogonal mRNA codons are extended codons or stop codons. Advantageously, the orthogonal mRNA codon is a quintuplet codon, a quadruplet codon or an amber stop codon.

Preferably the orthogonal mRNA comprises one or more amber stop codons, preferably two or more amber stop codons, preferably three or more amber stop codons, preferably four or more, amber stop codons, preferably five or more amber stop codons, preferably six or more amber stop codons, preferably seven or more amber stop codons, preferably ten or more amber stop codons, or even more. The advantage of these embodiment(s) is that in the prior art, multiple amber stop codons lead to a dramatic reduction in translation efficiency, whereas according to the present invention these mRNAs are translated at greatly enhanced efficiency. This advantage is correspondingly greater, the greater the number of amber stop codons present in the mRNA of interest.

The orthogonal rRNA of the present invention is preferably a 16S rRNA. 16S rRNA forms the A-site in the ribosome and is responsible for binding of the extended anticodon tRNA to the ribosome.

Preferably, the orthogonal rRNA of the invention is a mutated 16S rRNA. The 530 loop of 16S rRNA is proximal to the codon-anticodon helix; preferably, the mutated 16S rRNA is mutated in the 530 loop, between positions 529 and 535.

Preferably, the orthogonal 16S rRNA comprises A531G and U534A mutations. Advantageously this orthogonal 16S rRNA is incorporated into a mutant ribosome, which possesses A531G and U534A mutations, referred to herein as ribo-X.

According to a second aspect of the invention, there is provided a method for evolving an orthogonal rRNA molecule, comprising the steps of:
  (a) providing one or more libraries of mutant orthogonal rRNA molecules and introducing the libraries into cells such that the orthogonal rRNA is incorporated into ribosomes to provide orthogonal ribosomes;
  (b) providing one or more orthogonal mRNA molecules which (i) are not translated by natural ribosomes, and (ii) comprise one or more orthogonal mRNA codons;
  (c) assaying the translation of the of the orthogonal mRNA and selecting the orthogonal rRNA molecules which translate the orthogonal mRNA, wherein the assay in step (c) requires translation of one or more orthogonal mRNA codons in the orthogonal mRNA.

Preferably, the libraries of orthogonal rRNA molecules are libraries of 16S rRNA molecules, advantageously mutated in the 530 loop, between positions 529 and 535.

Preferably, the libraries of orthogonal rRNA molecules comprise A531G and U534A mutations.

Preferably, the orthogonal mRNA encodes a selectable marker; this marker may, for example, promote cell survival. Examples of selectable markers include chloramphenicol acetyltransferase, which allows the cell to survive exposure to chloramphenicol; cells which express CAT are thus selectable over cells that do not or do so less efficiently.

The orthogonal rRNA of the invention is useful in a variety of translation systems. For example, it can be used to improve systems which incorporate unnatural amino acids into cells. Accordingly, the invention provides a method for incorporating a unnatural amino acid into a polypeptide, comprising the steps of:
  (a) providing a mRNA molecule comprising a stop codon in a reading frame thereof, wherein read-though of the stop coding can result in the incorporation of a unnatural amino acid;
  (b) providing an orthogonal rRNA molecule according to any one of the claims, which reads the stop codon more efficiently than natural rRNA; and
  (c) using a suppressor tRNA to incorporate a unnatural amino acid into the polypeptide encoded by the mRNA molecule.

Preferably, the stop codon is a UAG amber stop codon; advantageously, the orthogonal rRNA molecule is an orthogonal rRNA molecule according to the first aspect of the invention.

In a further aspect, there is provided a cell comprising two or more protein translation mechanisms, wherein:
  (a) a first mechanism is the natural translation mechanism wherein mRNA is translated by a ribosome in accordance with the natural genetic code;
  (b) a second mechanism is an artificial mechanism, in which orthogonal mRNA comprising orthogonal codons is translated by an orthogonal ribosome;
  wherein the orthogonal codons in the orthogonal mRNA are
(i) not translated by the natural ribosome, or
(ii) translated less efficiently by the natural ribosome than by the orthogonal ribosome, or
(iii) translated into different polypeptides by the orthogonal ribosome and the natural ribosome.

The orthogonal codons are preferably extended codons, and advantageously quadruplet codons.

Alternatively, the orthogonal codons are stop codons, such as amber stop codons.

Preferably, the orthogonal ribosome in the cell incorporates an orthogonal rRNA according to the first aspect of the invention.

BRIEF DESCRIPTION OF THE FIGURES

FIG. 4. The effect of ribo-X on decoding quadruplet codons using several extended anticodon tRNAs derived from tRNAser2. For the progenitor O-ribosome and ribo-X the chloramphenicol resistance in mg ml-1 with O-cat (XXXX103, XXXX146)/tRNAser2(YYYY) is shown, along with the fold enhancement conferred by ribo-X. The data for UAGG, UAGC, UAGU and UAG codons are for a reporter with a single selector codon at position 103 in O-cat, because the activity was too low to measure accurately in the two codon construct.

FIG. 5. The efficiency of ribo-X in decoding the UAGA quadruplet codon. Thin-layer chromatography (TLC) showing the acetylation of chloramphenicol (Cm) to acetylated chloramphenicol (AcCm) by chloramphenicol acetyl transferase produced from either O-cat or O-cat (UAGA103, UAGA146).

FIG. 6. The specificity of ribo-X. A. Chloramphenicol resistance of cells containing O-cat (UAGN103, UAGN146)/tRNAser2(UCUA) and ribo-X. B. TLC labelled as in FIG. 5, using constructs as in FIG. 6 panel A.

FIG. 12 shows supplementary table 1.

FIG. 13 shows supplementary table 2.

DETAILED DESCRIPTION OF THE INVENTION

Definitions

Figure 1:
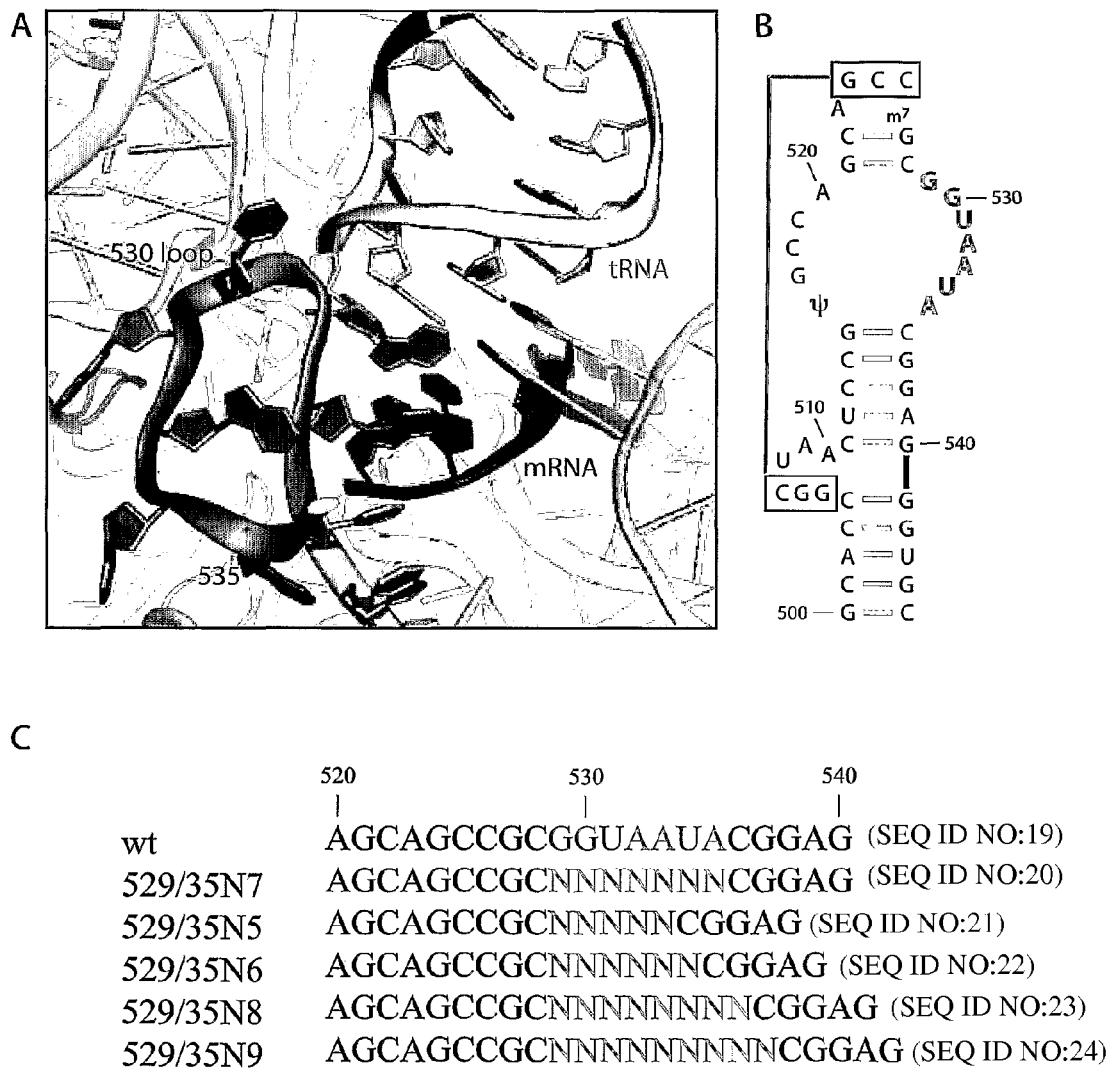
FIG. 1. Design of ribosome decoding libraries. A. Structure of a tRNA anticodon stem loop (yellow) bound to mRNA (purple) in the A site of the ribosome (green). The 530 loop is shown in orange. B. Secondary structure of the 530 loop. The boxed sequences form a pseudo knot, ψ is pseudouridine and m7G is 7-methyl guanosine. C. The sequence of ribosome decoding libraries. 3D structure figures were created using Pymol v0.99 and PDB ID 1IBM.

As the term "orthogonal" is used herein, it refers to a nucleic acid, for example rRNA or mRNA, which differs from natural, endogenous nucleic acid in its ability to cooperate with other nucleic acids. Orthogonal mRNA, rRNA and tRNA are provided in matched groups (cognate groups) which cooperate efficiently. For example, orthogonal rRNA, when part of a ribosome, will efficiently translate matched cognate orthogonal mRNA, but not natural, endogenous mRNA. For simplicity, a ribosome comprising an orthogonal rRNA is referred to herein as an "orthogonal ribosome," and an orthogonal ribosome will efficiently translate a cognate orthogonal mRNA.

An orthogonal codon or orthogonal mRNA codon is a codon in orthogonal mRNA which is only translated by a cognate orthogonal ribosome, or translated more efficiently, or differently, by a cognate orthogonal ribosome than by a natural, endogenous ribosome. Orthogonal is abbreviated to O (as in O-mRNA).

Thus, by way of example, orthogonal ribosome (O-ribosome)•orthogonal mRNA (O-mRNA) pairs are composed of: an mRNA containing a ribosome binding site that does not direct translation by the endogenous ribosome, and an orthogonal ribosome that efficiently and specifically translates the orthogonal mRNA, but does not appreciably translate cellular mRNAs.

"Evolved", as applied herein for example in the expression "evolved orthogonal ribosome", refers to the development of a function of a molecule through diversification and selection. For example, a library of rRNA molecules diversified at desired positions can be subjected to selection according to the procedures described herein. An evolved rRNA is obtained by the selection process.

As used herein, the term "mRNA" when used in the context of an O-mRNA O-ribosome pair refers to an mRNA that comprises an orthogonal codon which is efficiently translated by a cognate O-ribosome, but not by a natural, wild-type ribosome. In addition, it may comprise an mutant ribosome binding site (particularly the sequence from the AUG initiation codon upstream to −13 relative to the AUG) that efficiently mediates the initiation of translation by the O-ribosome, but not by a wild-type ribosome. The remainder of the mRNA can vary, such that placing the coding sequence for any protein downstream of that ribosome binding site will result in an mRNA that is translated efficiently by the orthogonal ribosome, but not by an endogenous ribosome.

As used herein, the term "rRNA" when used in the context of an O-mRNA O-ribosome pair refers to a rRNA mutated such that the rRNA is an orthogonal rRNA, and a ribosome containing it is an orthogonal ribosome, i.e., it efficiently translates only a cognate orthogonal mRNA. The primary, secondary and tertiary structures of wild-type ribosomal rRNAs are very well known, as are the functions of the various conserved structures (stems-loops, hairpins, hinges, etc.). O-rRNA typically comprises a mutation in 16S rRNA which is responsible for binding of tRNA during the translation process. It may also comprise mutations in the 3' regions of the small rRNA subunit which are responsible for the initiation of translation and interaction with the ribosome binding site of mRNA.

The expression of an "O-rRNA" in a cell, as the term is used herein, is not toxic to the cell. Toxicity is measured by cell death, or alternatively, by a slowing in the growth rate by 80% or more relative to a cell that does not express the "O-mRNA." Expression of an O-rRNA will preferably slow growth by less than 50%, preferably less than 25%, more preferably less than 10%, and more preferably still, not at all, relative to the growth of similar cells lacking the O-rRNA.

As used herein, the terms "more efficiently translates" and "more efficiently mediates translation" mean that a given O-mRNA is translated by a cognate O-ribosome at least 25% more efficiently, and preferably at least 2, 3, 4 or 8 or more times as efficiently as an O-mRNA is translated by a wild-type ribosome or a non-cognate O-ribosome in the same cell or cell type. As a gauge, for example, one may evaluate translation efficiency relative to the translation of an O-mRNA encoding chloramphenicol acetyl transferase using at least one orthogonal codon by a natural or non-cognate orthogonal ribosome.

As used herein, the term "corresponding to" when used in reference to nucleotide sequence means that a given sequence in one molecule, e.g., in a 16S rRNA, is in the same position in another molecule, e.g., a 16S rRNA from another species. By "in the same position" is meant that the "corresponding" sequences are aligned with each other when aligned using the BLAST sequence alignment algorithm "BLAST 2 Sequences" described by Tatusova and Madden (1999, "Blast 2 sequences—a new tool for comparing protein and nucleotide sequences", FEMS Microbiol. Lett. 174:247-250) and available from the U.S. National Center for Biotechnology Information (NCBI). To avoid any doubt, the BLAST version 2.2.11 (available for use on the NCBI website or, alternatively, available for download from that site) is used, with default parameters as follows: program, blastn; reward for a match, 1; penalty for a mismatch, −2; open gap and extend gap penalties 5 and 2, respectively; ga×dropoff, 50; expect 10.0; word size 11; and filter on.

As used herein, the term "selectable marker" refers to a gene sequence that permits selection for cells in a population that encode and express that gene sequence by the addition of a corresponding selection agent.

As used herein, the term "region comprising sequence that interacts with mRNA at the ribosome binding site" refers to a region of sequence comprising the nucleotides near the 3' terminus of 16S rRNA that physically interact, e.g., by base pairing or other interaction, with mRNA during the initiation of translation. The "region" includes nucleotides that base pair or otherwise physically interact with nucleotides in mRNA at the ribosome binding site, and nucleotides within five nucleotides 5' or 3' of such nucleotides. Also included in this "region" are bases corresponding to nucleotides 722 and 723 of the E. coli 16S rRNA, which form a bulge proximal to the minor groove of the Shine-Delgarno helix formed between the ribosome and mRNA.

As used herein, the term "diversified" means that individual members of a library will vary in sequence at a given site. Methods of introducing diversity are well known to those skilled in the art, and can introduce random or less than fully random diversity at a given site. By "fully random" is meant that a given nucleotide can be any of G, A, T, or C (or in RNA, any of G, A, U and C). By "less than fully random" is meant that a given site can be occupied by more than one different nucleotide, but not all of G, A, T (U in RNA) or C, for example where diversity permits either G or A, but not U or C, or permits G, A, or U but not C at a given site.

As used herein, the term "ribosome binding site" refers to the region of an mRNA that is bound by the ribosome at the initiation of translation. As defined herein, the "ribosome binding site" of prokaryotic mRNAs includes the Shine-Delgarno consensus sequence and nucleotides −13 to +1 relative to the AUG initiation codon.

As used herein, the term "unnatural amino acid" refers to an amino acid other than the amino acids that occur naturally in protein. Non-limiting examples include: a p-acetyl-L-phenylalanine, a p-iodo-L-phenylalanine, an O-methyl-L-tyrosine, a p-propargyloxyphenylalanine, a p-propargyl-phenylalanine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-bromophenylalanine, a p-amino-L-phenylalanine, an isopropyl-L-phenylalanine, an unnatural analogue of a tyrosine amino acid; an unnatural analogue of a glutamine amino acid; an unnatural analogue of a phenylalanine amino acid; an unnatural analogue of a serine amino acid; an unnatural analogue of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, or amino substituted amino acid, or a combination thereof; an amino acid with a photoactivatable cross-linker; a spin-labeled amino acid; a fluorescent amino acid; a metal binding amino acid; a metal-containing amino acid; a radioactive amino acid; a photocaged and/or photoisomerizable amino acid; a biotin or biotin-analogue containing amino acid; a keto containing amino acid; an amino acid comprising polyethylene glycol or polyether; a heavy atom substituted amino acid; a chemically cleavable or photocleavable amino acid; an amino acid with an elongated side chain; an amino acid containing a toxic group; a sugar substituted amino acid; a carbon-linked sugar-containing amino acid; a redox-active amino acid; an α-hydroxy containing acid; an amino thio acid; an α,α disubstituted amino acid; a β-amino acid; a cyclic amino acid other than proline or histidine, and an aromatic amino acid other than phenylalanine, tyrosine or tryptophan.

In our copending international patent application PCT/GB2006/002637 we describe the generation of orthogonal ribosome/mRNA pairs in which the ribosome binding site in the O-mRNA binds specifically to the O-ribosome.

Briefly, the bacterial ribosome is a 2.5 MDa complex of rRNA and protein responsible for translation of mRNA into protein (The Ribosome, Vol. LXVI. (Cold Spring Harbor Laboratory Press, Cold Spring Harbor, N.Y.; 2001). The interaction between the mRNA and the 30S subunit of the ribosome is an early event in translation (Laursen, B. S., Sorensen, H. P., Mortensen, K. K. & Sperling-Petersen, H. U., *Microbiol Mol Biol Rev* 69, 101-123 (2005)), and several features of the mRNA are known to control the expression of a gene, including the first codon (Wikstrom, P. M., Lind, L. K., Berg, D. E. & Bjork, G. R., *J Mol Biol* 224, 949-966 (1992)), the ribosome-binding sequence (including the Shine Delgarno (SD) sequence (Shine, J. & Delgarno, L., *Biochem J* 141, 609-615 (1974), Steitz, J. A. & Jakes, K., *Proc Natl Acad Sci USA* 72, 4734-4738 (1975), Yusupova, G. Z., Yusupov, M. M., Cate, J. H. & Noller, H. F., *Cell* 106, 233-241 (2001)), and the spacing between these sequences (Chen, H., Bjerknes, M., Kumar, R. & Jay, E., *Nucleic Acids Res* 22, 4953-4957 (1994)). In certain cases mRNA structure (Gottesman, S. et al. in The Ribosome, Vol. LXVI (Cold Spring Harbor Laboratory Press, Cold Spring Harbor, N.Y.; 2001), Looman, A. C., Bodlaender, J., de Gruyter, M., Vogelaar, A. & van Knippenberg, P. H., *Nucleic Acids Res* 14, 5481-5497 (1986)), Liebhaber, S. A., Cash, F. & Eshleman, S. S., *J Mol Biol* 226, 609-621 (1992), or metabolite binding (Winkler, W., Nahvi, A. & Breaker, R. R., *Nature* 419, 952-956 (2002)), influences translation initiation, and in rare cases mRNAs can be translated without a SD sequence, though translation of these sequences is inefficient (Laursen, B. S., Sorensen, H. P., Mortensen, K. K. & Sperling-Petersen, H. U., *Microbiol Mol Biol Rev* 69, 101-123 (2005)), and operates through an alternate initiation pathway, Laursen, B. S., Sorensen, H. P., Mortensen, K. K. & Sperling-Petersen, H. U. Initiation of protein synthesis in bacteria. *Microbiol Mol Biol Rev* 69, 101-123 (2005). For the vast majority of bacterial genes the SD region of the mRNA is a major determinant of translational efficiency. The classic SD sequence GGAGG interacts through RNA-RNA base-pairing with a region at the 3' end of the 16S rRNA containing the sequence CCUCC, known as the Anti Shine Delgarno (ASD). In *E. coli* there are an estimated 4,122 translational starts (Shultzaberger, R. K., Bucheimer, R. E., Rudd, K. E. & Schneider, T. D., *J Mol Biol* 313, 215-228 (2001)), and these differ in the spacing between the SD-like sequence and the AUG start codon, the degree of complementarity between the SD-like sequence and the ribosome, and the exact region of sequence at the 3' end of the 16S rRNA with which the mRNA interacts. The ribosome therefore drives translation from a more complex set of sequences than just the classic Shine Delgarno (SD) sequence. For clarity, mRNA sequences believed to bind the 3' end of 16S rRNA are referred to as SD sequences and to the specific sequence GGAGG is referred to as the classic SD sequence.

Mutations in the SD sequence often lead to rapid cell lysis and death (Lee, K., Holland-Staley, C. A. & Cunningham, P. R., *RNA* 2, 1270-1285 (1996), Wood, T. K. & Peretti, S. W., *Biotechnol. Bioeng* 38, 891-906 (1991)). Such mutant ribosomes mis-regulate cellular translation and are not orthogonal. The sensitivity of cell survival to mutations in the ASD region is underscored by the observation that even a single change in the ASD can lead to cell death through catastrophic and global mis-regulation of proteome synthesis (Jacob, W. F., Santer, M. & Dahlberg, A. E., *Proc Natl Acad Sci USA* 84, 4757-4761 (1987). Other mutations in the rRNA can lead to inadequacies in processing or assembly of functional ribosomes.

PCT/GB2006/02637 describes methods for tailoring the molecular specificity of duplicated *E. coli* ribosome mRNA pairs with respect to the wild-type ribosome and mRNAs to produce multiple orthogonal ribosome orthogonal mRNA pairs. In these pairs the ribosome efficiently translates only the orthogonal mRNA and the orthogonal mRNA is not an efficient substrate for cellular ribosomes. Orthogonal ribosomes as described therein that do not translate endogenous mRNAs permit specific translation of desired cognate mRNAs without interfering with cellular gene expression. The network of interactions between these orthogonal pairs is predicted and measured, and it is shown that orthogonal ribosome mRNA pairs can be used to post-transcriptionally program the cell with Boolean logic.

PCT/GB2006/02637 describes a mechanism for positive and negative selection for evolution of orthogonal translational machinery. The selection methods are applied to evolving multiple orthogonal ribosome mRNA pairs (O-ribosome O-mRNA). Also described is the successful prediction of the network of interactions between cognate and non-cognate O-ribosomes and O-mRNAs.

Here we provide new, further modified orthogonal ribosomes and methods for producing such O-ribosomes which expand the molecular decoding properties of the ribosome. Specifically, we evolve orthogonal ribosomes that more efficiently decode a set of quadruplet codons using tRNAs with extended anticodon loops. Moreover, we provide a mechanistic explanation of the enhancements we observe, and demonstrate that the evolved orthogonal ribosome is also substantially more efficient at decoding amber codons with amber suppressor tRNAs.

We disclose evolved orthogonal ribosomes which enhance the efficiency of synthetic genetic code expansion. We provide cellular modules composed of an orthogonal ribosome and an orthogonal mRNA. These pairs function in parallel with, but independent of, the natural ribosome-mRNA pair in *Escherichia coli*. Orthogonal ribosomes do not synthesize the proteome and may be diverged to operate using different tRNA decoding rules from natural ribosomes. Here we demonstrate the evolution of an orthogonal ribosome (ribo-X) for the efficient, high fidelity decoding of codons such as amber codons placed within the context of an orthogonal mRNA in living cells. We combine ribo-X, orthogonal mRNAs and orthogonal aminoacyl-tRNA synthetase/tRNA pairs to substantially increase the efficiency of site-specific unnatural amino acid incorporation in *E. coli*. This advantageously allows the efficient synthesis of proteins incorporating unnatural amino acids at multiple sites, and/or minimizes the functional and/or phenotypic effects of truncated proteins for example in experiments that use unnatural amino acid incorporation to probe protein function in vivo.

Orthogonal Codons

For the first time, we describe an evolved ribosome which is capable of translating an orthogonal mRNA codon, which means that the ribosome interprets mRNA information according to a code which is not the universal genetic code, but an orthogonal genetic code. This introduces a number of possibilities, including the possibility of having two separate genetic systems present in the cell, wherein cross-talk is eliminated by virtue of the difference in code; or of a mRNA molecule encoding different polypeptides according to which code is used to translate it.

An orthogonal codon, from which orthogonal genetic codes can be assembled, is a code which is other than the universal triplet code. Table 1 below represents the universal genetic code:

TABLE 1

| | | Second nucleotide | | | |
|---|---|---|---|---|---|
| | U | C | A | G | |
| U | UUU Phenylalanine (Phe) | UCU Serine (Ser) | UAU Tyrosine (Tyr) | UGU Cysteine (Cys) | U |
| | UUC Phe | UCC Ser | UAC Tyr | UGC Cys | C |
| | UUA Leucine (Leu) | UCA Ser | UAA STOP | UGA STOP | A |
| | UUG Leu | UCG Ser | UAG STOP | UGG Tryptophan (Trp) | G |
| C | CUU Leucine (Leu) | CCU Proline (Pro) | CAU Histidine (His) | CGU Arginine (Arg) | U |
| | CUC Leu | CCC Pro | CAC His | CGC Arg | C |
| | CUA Leu | CCA Pro | CAA Glutamine (Gln) | CGA Arg | A |
| | CUG Leu | CCG Pro | CAG Gln | CGG Arg | G |
| A | AUU Isoleucine (Ile) | ACU Threonine (Thr) | AAU Asparagine (Asn) | AGU Serine (Ser) | U |
| | AUC Ile | ACC Thr | AAC Asn | AGC Ser | C |
| | AUA Ile | ACA Thr | AAA Lysine (Lys) | AGA Arginine (Arg) | A |
| | AUG Methionine (Met) or START | ACG Thr | AAG Lys | AGG Arg | G |
| G | GUU Valine Val | GCU Alanine (Ala) | GAU Aspartic acid (Asp) | GGU Glycine (Gly) | U |
| | GUC (Val) | GCC Ala | GAC Asp | GGC Gly | C |
| | GUA Val | GCA Ala | GAA Glutamic acid (Glu) | GGA Gly | A |
| | GUG Val | GCG Ala | GAG Glu | GGG Gly | G |

Certain variations in this code occur naturally; for example, mitochondria use UGA to encode tryptophan (Trp) rather than as a chain terminator. In addition, most animal mitochondria use AUA for methionine not isoleucine and all vertebrate mitochondria use AGA and AGG as chain terminators.

Yeast mitochondria assign all codons beginning with CU to threonine instead of leucine (which is still encoded by UUA and UUG as it is in cytosolic mRNA).

Plant mitochondria use the universal code, and this has permitted angiosperms to transfer mitochondrial genes to their nucleus with great ease.

Violations of the universal code are far rarer for nuclear genes. A few unicellular eukaryotes have been found that use one or two (of their three) STOP codons for amino acids instead.

The vast majority of proteins are assembled from the 20 amino acids listed above even though some of these may be chemically altered, e.g. by phosphorylation, at a later time.

However, two cases have been found in nature where an amino acid that is not one of the standard 20 is inserted by a tRNA into the growing polypeptide.

Selenocysteine. This amino acid is encoded by UGA. UGA is still used as a chain terminator, but the translation machinery is able to discriminate when a UGA codon should be used for selenocysteine rather than STOP. This codon usage has been found in certain Archaea, eubacteria, and animals (humans synthesize 25 different proteins containing selenium).

Pyrrolysine. In one gene found in a member of the Archaea, this amino acid is encoded by UAG. How the translation machinery knows when it encounters UAG whether to insert a tRNA with pyrrolysine or to stop translation is not yet known.

All of the above are, for the purposes of the present invention, considered to be part of the universal genetic code.

The present invention enables novel codes, not previously known in nature, to be developed and used in the context of orthogonal mRNA/rRNA pairs.

Selection for Orthogonal Ribosomes

A selection approach for the identification of orthogonal ribosome orthogonal mRNA pairs, or other pairs of orthogonal molecules, requires selection for translation of orthogonal codons in O-mRNA. The selection is advantageously positive selection, such that cells which express O-mRNA are selected over those that do not, or do so less efficiently.

A number of different positive selection agents can be used. The most common selection strategies involve conditional survival on antibiotics. Of these positive selections, the chloramphenicol acetyl-transferase gene in combination with the antibiotic chloramphenicol has proved one of the most useful. Others as known in the art, such as ampicillin, kanamycin, tetracycline or streptomycin resistance, among others, can also be used.

O-mRNA/O-rRNA pairs can be used to produce an orthogonal transcript in a host cell, for example CAT, that can only be translated by the cognate orthogonal ribosome, thereby permitting extremely sensitive control of the expression of a polypeptide encoded by the transcript. The pairs can thus be used to produce a polypeptide of interest by, for example, introducing nucleic acid encoding such a pair to a cell, where the orthogonal mRNA encodes the polypeptide of interest. The translation of the orthogonal mRNA by the orthogonal ribosome results in production of the polypeptide of interest. It is contemplated that polypeptides produced in cells encoding orthogonal mRNA orthogonal ribosome pairs can include unnatural amino acids.

The methods described herein are applicable to the selection of orthogonal mRNA orthogonal rRNA pairs in species in which the O-mRNA comprises orthogonal codons which are translated by the O-rRNA. Thus, the methods are broadly applicable across prokaryotic and eukaryotic species, in which this mechanism is conserved. The sequence of 16S rRNA is known for a large number of bacterial species and has itself been used to generate phylogenetic trees defining the evolutionary relationships between the bacterial species (reviewed, for example, by Ludwig & Schleifer, 1994, FEMS Microbiol. Rev. 15: 155-73; see also Bergey's Manual of Systematic Bacteriology Volumes 1 and 2, Springer, George M. Garrity, ed.). The Ribosomal Database Project II (Cole J R, Chai B, Farris R J, Wang Q, Kulam S A, McGarrell D M, Garrity G M, Tiedje J M, *Nucleic Acids Res*, (2005) 33(Database Issue):D294-D296. doi: 10.1093/nar/gki038) provides, in release 9.28 (Jun. 17, 2005), 155,708 aligned and annotated 16S rRNA sequences, along with online analysis tools.

Phylogenetic trees are constructed using, for example, 16S rRNA sequences and the neighbour joining method in the ClustalW sequence alignment algorithm. Using a phylogenetic tree, one can approximate the likelihood that a given set of mutations (on 16S rRNA and a codon in mRNA) that render the set orthogonal with respect to each other in one species will have a similar effect in another species. Thus, the mutations rendering mRNA/16S rRNA pairs orthogonal with respect to each other in one member of, for example, the Enterobacteriaceae Family (e.g., *E. coli*) would be more likely to result in orthogonal mRNA/orthogonal ribosome pairs in another member of the same Family (e.g., *Salmonella*) than in a member of a different Family on the phylogenetic tree.

In some instances, where bacterial species are very closely related, it may be possible to introduce corresponding 16S rRNA and mRNA mutations that result in orthogonal molecules in one species into the closely related species to generate an orthogonal mRNA orthogonal rRNA pair in the related species. Also where bacterial species very are closely related (e.g., for *E. coli* and *Salmonella* species), it may be possible to introduce orthogonal 16S rRNA and orthogonal mRNA from one species directly to the closely related species to obtain a functional orthogonal mRNA orthogonal ribosome pair in the related species.

Alternatively, where the species in which one wishes to identify orthogonal mRNA orthogonal ribosome pairs is not closely related (e.g., where they are not in the same phylogenetic Family) to a species in which a set of pairs has already been selected, one can use selection methods as described herein to generate orthogonal mRNA orthogonal ribosome pairs in the desired species. Briefly, one can prepare a library of mutated orthogonal 16S rRNA molecules. The library can then be introduced to the chosen species. One or more O-mRNA sequences can be generated which comprise a sequence encoding a selection polypeptide as described herein using one or more orthogonal codons (the bacterial species must be sensitive to the activity of the selection agents, a matter easily determined by one of skill in the art). The O-mRNA library can then be introduced to cells comprising the O-rRNA library, followed by positive selection for those cells expressing the positive selectable marker in order to identify orthogonal ribosomes that pair with the O-mRNA.

The methods described herein are applicable to the identification of molecules useful to direct translation or other processes in a wide range of bacteria, including bacteria of industrial and agricultural importance as well as pathogenic bacteria. Pathogenic bacteria are well known to those of skill in the art, and sequence information, including not only 16S rRNA sequence, but also numerous mRNA coding sequences, are available in public databases, such as GenBank. Common, but non-limiting examples include, e.g., *Salmonella* species, *Clostridium* species, e.g., *Clostridium botulinum* and *Clostridium perfringens*, *Staphylococcus* sp., e.g, *Staphylococcus aureus*; *Campylobacter* species, e.g., *Campylobacter jejuni*, *Yersinia* species, e.g., *Yersinia pestis*, *Yersinia enterocolitica* and *Yersinia pseudotuberculosis*, *Listeria* species, e.g., *Listeria monocytogenes*, *Vibrio* species, e.g., *Vibrio cholerae*, *Vibrio parahaemolyticus* and *Vibrio vulnificus*, *Bacillus cereus*, *Aeromonas* species, e.g., *Aeromonas hydrophila*, *Shigella* species, *Streptococcus* species, e.g., *Streptococcus pyogenes*, *Streptococcus faecalis*, *Streptococcus faecium*, *Streptococcus pneumoniae*, *Streptococcus durans*, and *Streptococcus avium*, *Mycobacterium tuberculosis*, *Klebsiella* species, *Enterobacter* species, *Proteus* species, *Citrobacter* species, *Aerobacter* species, *Providencia* species, *Neisseria* species, e.g., *Neisseria gonorrhea* and *Neisseria meningitidis*, *Heamophilus* species, e.g., *Haemophilus influenzae*, *Helicobacter* species, e.g., *Helicobacter pylori*, *Bordetella* species, e.g., *Bordetella pertussis*, *Serratia* species, and pathogenic species of *E. coli*, e.g., Enterotoxigenic *E. coli* (ETEC), enteropathogenic *E. coli* (EPEC) and enterohemorrhagic *E. coli* O157:H7 (EHEC).

Release Factor 1/Amber Codons

Figure 7:
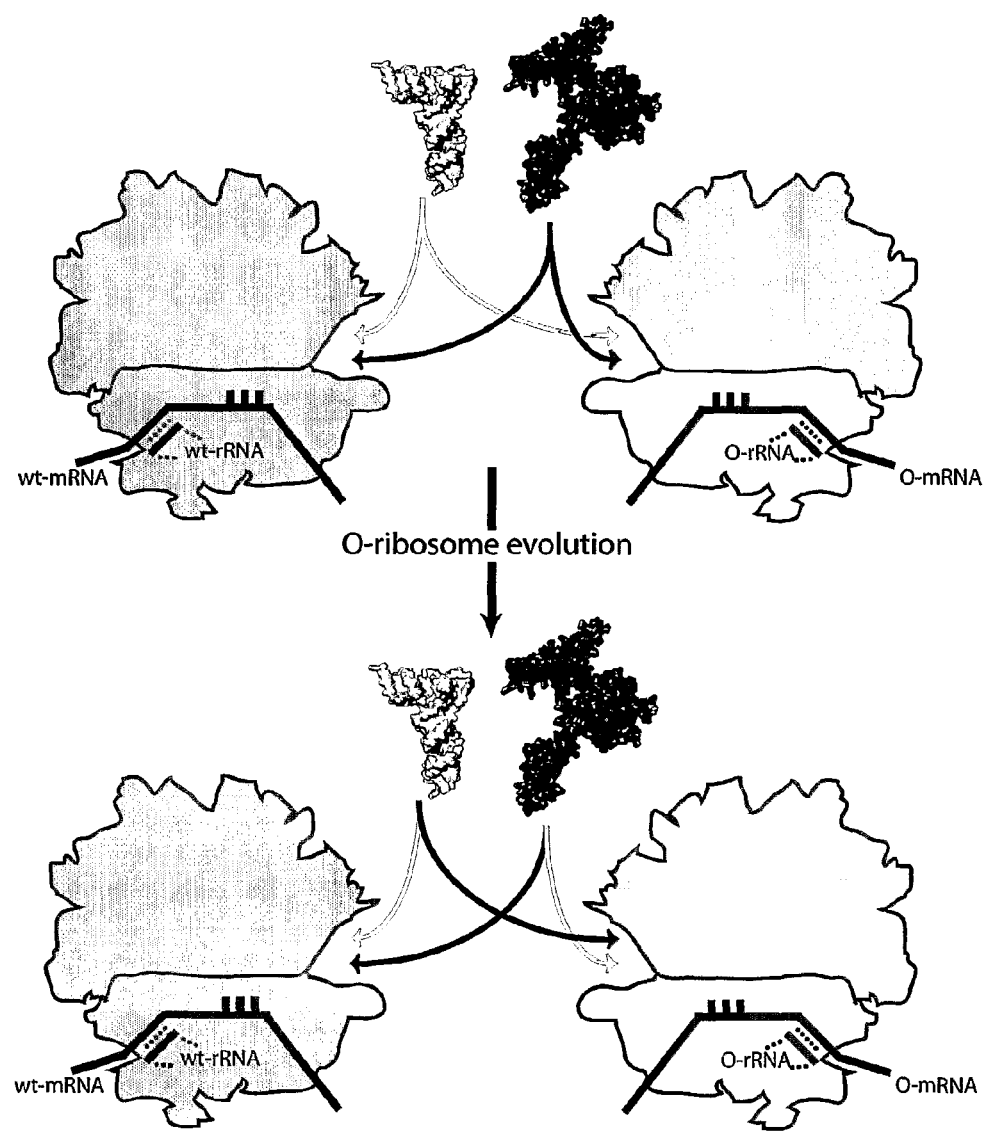
FIG. 7. Diverging the decoding properties of natural and orthogonal ribosomes. The natural ribosome (grey) and the progenitor orthogonal ribosome (green) decode wt-(black) and orthogonal-(purple) mRNAs respectively. Because RF-1 (blue) competes efficiently (dark grey arrows) for UAG codons in the A-site of both ribosomes, amber suppressor tRNAs (yellow), that may be uniquely aminoacylated with an unnatural amino acid, are decoded with equal and low efficiency (light grey arrows) on both ribosomes. Synthetic evolution of the orthogonal ribosome leads to an evolved scenario in which a mutant (orange patch) orthogonal ribosome more efficiently decodes amber suppressor tRNAs within the context of orthogonal mRNAs. Decoding of natural mRNAs is unaffected because the orthogonal ribosome does not read natural mRNAs and the natural ribosome is unaltered. Surface structure figures are created using Pymol v0.99 and PDB IDs 2B64 and 1J1U.

Advantageously, to maximize the efficiency of full-length protein synthesis with respect to truncated protein, the effects of release factor 1 (RF-1)-mediated chain termination would be minimized for the expression of a gene of interest, while the decoding of chromosomal amber stop codons would remain unaltered. We conceived to use recently described orthogonal ribosome-mRNA pairs to address this challenge (see examples and FIG. 7).

Unlike the natural ribosome the orthogonal ribosome is not responsible for synthesizing the proteome, and is therefore tolerant to mutations in the highly conserved rRNA that cause lethal or dominant negative effects in the natural ribosome. Orthogonal ribosomes may therefore be advantageously evolved towards decreased RF-1 binding and increased tRNA dependent amber suppression according to the present invention. Moreover, increased amber suppression within the context of an orthogonal ribosome has the advantage of operating on amber codons within orthogonal mRNAs whilst advantageously also not increasing suppression of chromosomal stop codons.

We disclose the synthetic evolution of an orthogonal ribosome (ribo-X) for the efficient, high fidelity, suppressor tRNA dependent decoding of amber stop codons placed within the context of an orthogonal mRNA in living cells. Ribo-X may preferably be combined with orthogonal mRNAs and orthogonal aminoacyl-tRNA synthetase/tRNA$_{CUA}$ pairs to advantageously significantly increase the efficiency of site-specific unnatural amino acid incorporation in E. coli. This increase in efficiency makes it possible to synthesize proteins incorporating unnatural amino acids at multiple sites, and minimizes the functional and phenotypic effects of truncated proteins in vivo. This has clear industrial application and utility, for example in the manufacture of proteins incorporating unnatural amino acids.

Since ribo-X increases suppression of amber stop codons by suppressor tRNAs of distinct sequence and structure, we suggest that ribo-X operates by decreasing its functional interaction with RF-1, allowing the suppressor tRNAs to more efficiently compete for A-site binding in the presence of a UAG codon on the mRNA. Variations or optimisation of the strategy disclosed here may yield further increases in amber suppression while maintaining translational fidelity. In this regard it is encouraging both that biochemical evidence suggests distinct conformations of the decoding centre are recognized by tRNAs and RF-1 (Youngman et al Cold Spring Harb Symp Quant Biol 71, 545-549 (2006)) and that we have been able to select combinations of mutations for which RF-1 mediated termination is decreased without decreasing the fidelity of tRNA decoding. These observations surprisingly indicate that the molecular determinants for the fidelity of tRNA decoding and RF-1 binding need not be tightly coupled and thus further independent modulation within the orthogonal system is enabled by the present invention.

By improving amber suppression efficiency on the orthogonal ribosome it is now possible to diverge the decoding properties of the orthogonal ribosome from those of the cellular ribosome such that the same insertion signal is read with a different efficiency on cellular and orthogonal mRNAs within the same cell as demonstrated herein. A conceptually similar, but mechanistically distinct, strategy involving localization of specialized translational components is used by nature to direct the incorporation of selenocysteine in response to a subset of UGA codons. Thus the invention may find application in similar strategies to enhance the efficiency of synthetic eukaryotic genetic code expansion. Since the meaning of codons on any mRNA are set by the translational machinery that decodes that mRNA, it may be possible to use our approach to write entirely new genetic codes on orthogonal mRNAs and to undo the "frozen accident" of the existing genetic code. For example, it may be possible to use tRNAs that are poor substrates for the cellular ribosome but are efficiently decoded by evolved orthogonal ribosomes to write independent and parallel codes (orthogonal genetic codes). Orthogonal genetic codes may form a basis for a biological "virtual operating system" that further expands the information storage and genetic encoding capacity of the cell.

Bacterial Transformation

The methods described herein rely upon the introduction of foreign or exogenous nucleic acids into bacteria. Methods for bacterial transformation with exogenous nucleic acid, and particularly for rendering cells competent to take up exogenous nucleic acid, is well known in the art. For example, Gram negative bacteria such as E. coli are rendered transformation competent by treatment with multivalent cationic agents such as calcium chloride or rubidium chloride. Gram positive bacteria can be incubated with degradative enzymes to remove the peptidoglycan layer and thus form protoplasts. When the protoplasts are incubated with DNA and polyethylene glycol, one obtains cell fusion and concomitant DNA uptake. In both of these examples, if the DNA is linear, it tends to be sensitive to nucleases so that transformation is most efficient when it involves the use of covalently closed circular DNA. Alternatively, nuclease-deficient cells (RecBC⁻ strains) can be used to improve transformation.

Electroporation is also well known for the introduction of nucleic acid to bacterial cells. Methods are well known, for example, for electroporation of Gram negative bacteria such as E. coli, but are also well known for the electroporation of Gram positive bacteria, such as Enterococcus faecalis, among others, as described, e.g., by Dunny et al., 1991, Appl. Environ. Microbiol. 57: 1194-1201.

EXAMPLES

Example 1

Evolution of an Orthogonal Ribosome

Design of a Ribosome Decoding Centre Library for Enhanced Quadruplet Decoding

While the detailed mechanism of quadruplet decoding is controversial[17, 25] and may differ for different tRNA/codon pairs, it is clear that an early and essential step in decoding is the binding of the extended anticodon tRNA to the A-site of the ribosome in response to the quadruplet codon. Since the A-site is the gateway to the tRNA translocation corridor composed of the A, P and E sites[26-28], and is the primary site of codon-anticodon proofreading for elongator tRNAs[29], we reasoned that combinations of mutations in 16S rRNA, which forms the A-site, might yield an variant A-site that functions more efficiently with an extended anticodon loop tRNA.

To design an A-site library we examined the structures of normal tRNA anticodon stem loops bound to the ribosomal A site[27, 28, 30]. These structures show that the 530 loop in 16S rRNA is proximal to, and intimately associated with, the codon-anticodon helix (FIG. 1). We therefore randomized the seven nucleotides 529-535 in the 530 loop to all combinations of nucleotides to create an N7 library (FIG. 1). Moreover, we reasoned that since the extended tRNA anticodon contains an additional nucleotide, shorter 530 loop sequences in 16S rRNA might provide more space to accommodate the extended anticodon whereas longer 530 loop sequences might provide greater flexibility for the rRNA to adapt to the extended anticodon. We therefore created four additional libraries (N5, N6, N8, and N9 (FIG. 1)) All libraries created were more than 99% complete as determined by Poisson sampling statistics.

Selection for Orthogonal Ribosomes with Enhanced Quadruplet Decoding

Figure 2:
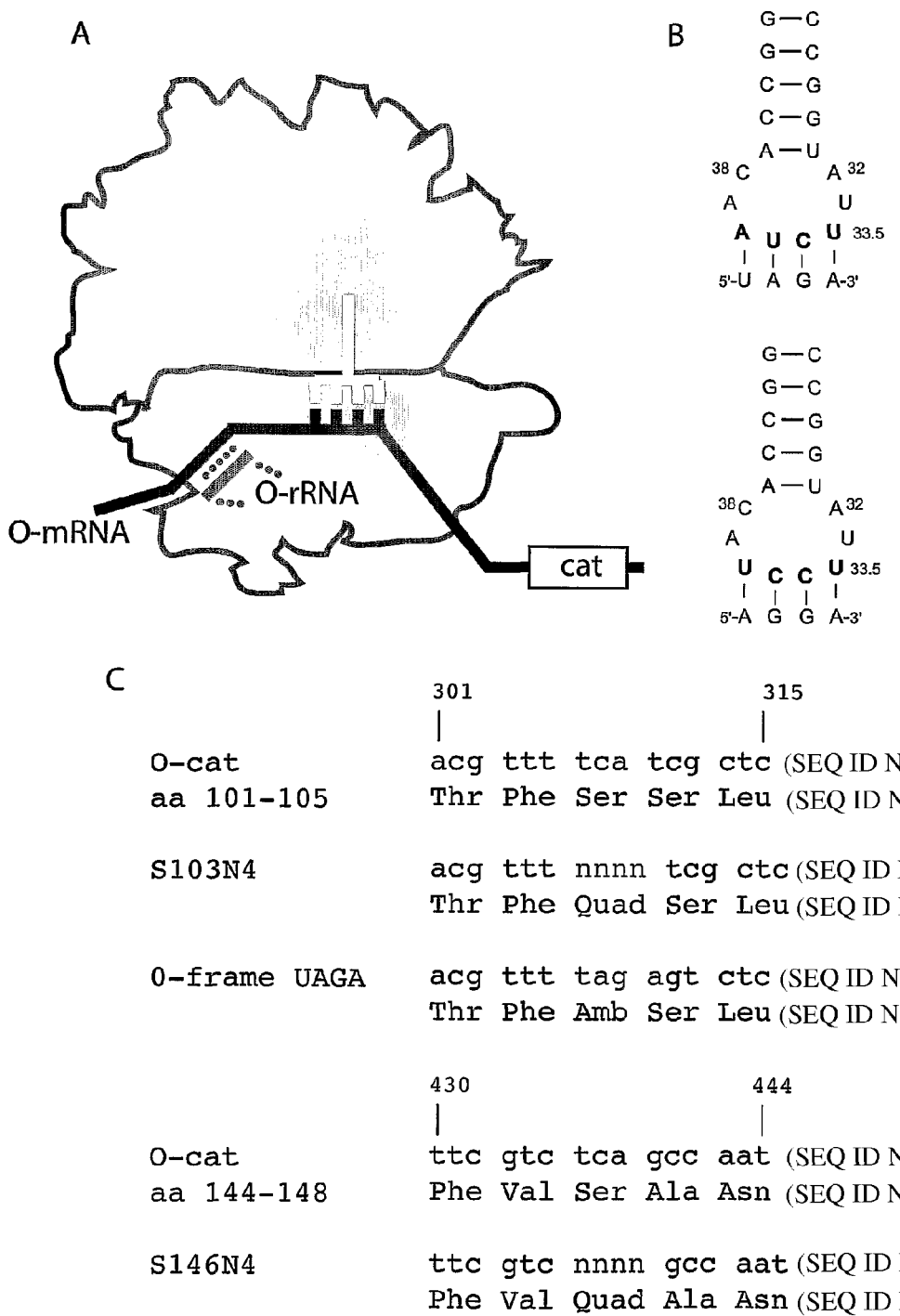
FIG. 2: Selection of orthogonal ribosomes for improved decoding of quadruplet codons. A. Schematic of the selection. Quadruplet codons on an orthogonal chloramphenicol acetyl transferase mRNA (purple) are decoded by orthogonal ribosomes (green) using extended anticodon tRNAs (yellow). The fidelity of incorporation is ensured by using serine inserting tRNAs and quadruplet codons at sites in the protein that require serine. Cells containing ribosome library members with improved quadruplet decoding are selected on chloramphenicol.
B. The anticodon stem loop sequences of the UAGA and UCCU decoding tRNAs used. C. The sequence surrounding the quadruplet codons in O-cat. The variable quadruplet codons "Quad" are denoted "nnnn". The O-frame UAGA sequence shows the mutations made to test the competition between quadruplet and triplet decoding.

To create a selection system for ribosomes that more efficiently read a quadruplet codon we required a reporter of orthogonal ribosome activity that contains selector quadruplet codons. We introduced the quadruplet codons (either UAGA or AGGA) at two sites in chloramphenicol acetyl transferase (cat) gene (Ser103 and Ser 146, an essential and conserved catalytic serine residue[31] that insures the fidelity of incorporation) downstream of an orthogonal ribosome binding site (FIG. 2). We combined the resulting reporters with well-characterized UCUA or UCCU anticodon tRNAs derived from tRNA$^{ser2}$ (FIG. 2), previously selected by Magliery et al[8]. Cells containing O-cat (UAGA103, UAGA146)/tRNA$^{ser2}$ (UCUA) and the O-ribosome had an IC$_{50}$ on chloramphenicol of 25 mg ml$^{-1}$, and cells containing O-cat (AGGA103, AGGA146)/tRNA$^{ser2}$ (UCCU) had an IC$_{50}$ on chloramphenicol of 80 mg ml$^{-1}$. For comparison the wild-type O-cat supports growth to 500 mg ml$^{-1}$ chloramphenicol in the presence of a cognate O-ribosome.

Figure 3:
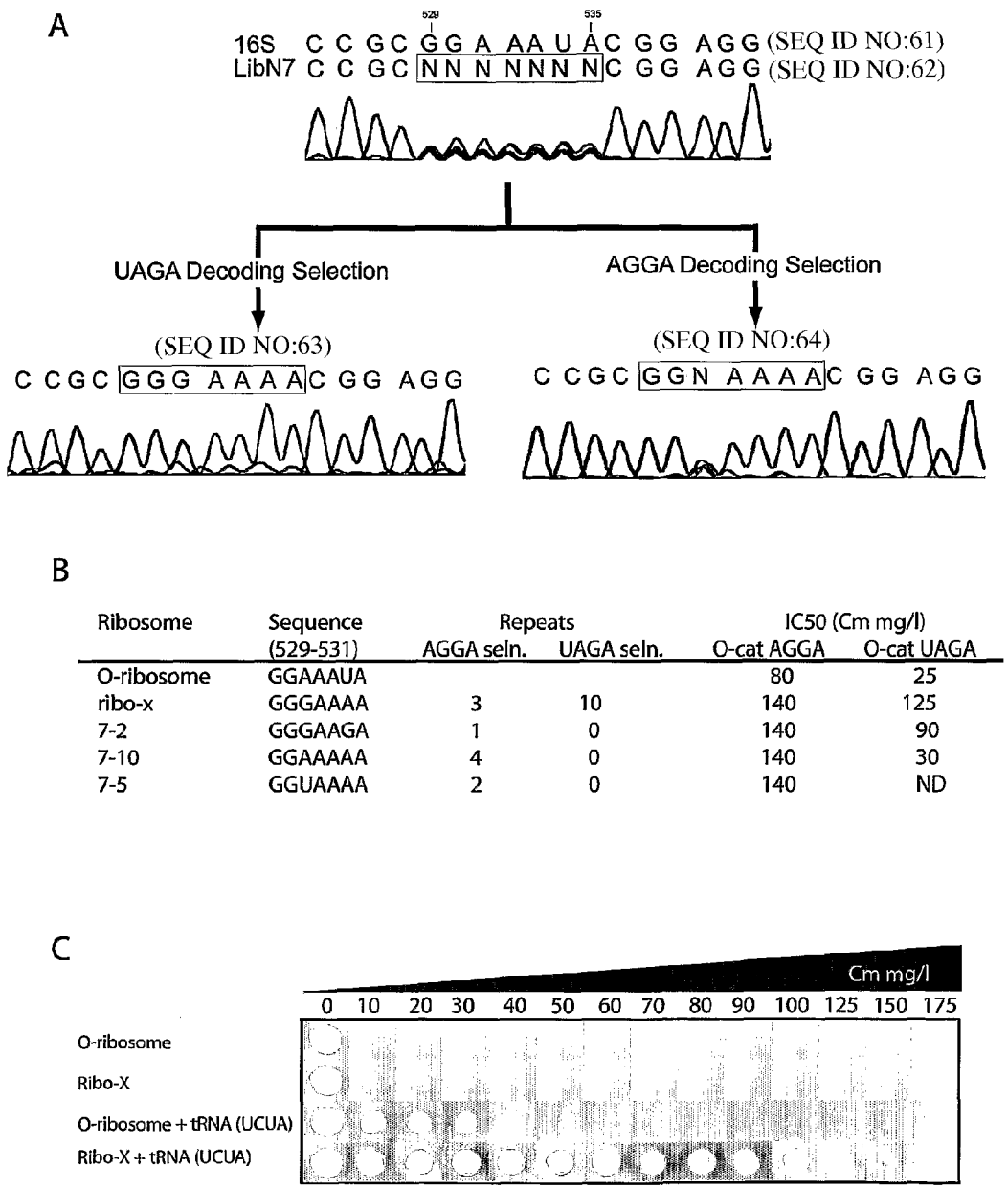
FIG. 3. Selection and characterization of ribosomes with enhanced tRNA dependent decoding of quadruplet codons A. The selection of ribosomes that decode UAGA and AGGA codons, using cognate tRNAs derived from tRNAser2. The top sequence trace shows the 16S rDNA before selection, while the lower traces show the convergence of the pool (sequencing from all colonies surviving a selection on chloramphenicol plates). B. The sequences of individual clones isolated from each selection and the enhancement in ribosome decoding of UAGA or AGGA codons with cognate tRNAs in O-cat (xxxx103,xxxx146)/tRNAser2(yyyy). C. The enhancement in decoding UAGA codons in the O-cat (UAGA103,UAGA146) gene with ribo-X is dependent on tRNAser2(UCUA).

To select mutant ribosomes that more efficiently decode the UAGA codon we combined each orthogonal ribosome library (N5-N9) with O-cat (UAGA103, UAGA146)/tRNA$^{ser2}$ (UCUA) and challenged the cells to grow on chloramphenicol concentrations at which the O-ribosome does not support growth (FIG. 2). While no clones containing insertions or deletions survived for libraries N5, N6, N8 and N9, suggesting that the 530 loop is intolerant to longer or shorter sequences of any composition, clones did survive from the N7 library on 50 mg ml$^{-1}$ chloramphenicol. We isolated and sequenced ten plasmids encoding surviving N7 library members. For the UAGA decoding selection, all clones sequenced were identical, and contained the mutations A531G and U534A. (FIG. 3). Next, we repeated the selection using the AGGA reporter and cognate tRNA. In this selection we found that the library also converges, to sequences similar to, and in some cases identical to, the sequence selected for decoding UAGA (FIG. 3). We combined the ribosomes from both selections with either the AGGA or UAGA reporters and found that, as expected, the UAGA selected ribosome decodes UAGA most efficiently. We also found that the UAGA selected ribosome is among the most efficient ribosomes for AGGA decoding. We therefore decided to characterize the A531G, U534A mutant ribosome, which we refer to as ribo-X, in more detail.

Example 2

Analysis of Ribo-X

Ribo-X Enhances tRNA Dependent Reading of UAGA Quadruplet Codons

To investigate whether ribo-X reads quadruplet codons in a tRNA dependent manner, we co-transformed ribo-X and O-cat (UAGA103, UAGA146) and measured chloramphenicol resistance. We find that ribo-X does not significantly contribute to +1 frame shifting in the absence of an extended anticodon tRNA (Cm resistance <1 mg ml$^{-1}$) (FIG. 3).

To measure the extent to which ribo-X enhances tRNA$^{ser2}$ (UCUA) dependent decoding of the UAGA codon we compared the chloramphenicol resistance of cells transformed with O-cat (UAGA103, UAGA146)/tRNA$^{ser2}$ (UCUA) and either ribo-X or the progenitor O-ribosome. We find that the ribo-X containing cells survive on concentrations of chloramphenicol five times higher (125 mg ml$^{-1}$) than cells containing the progenitor O-ribosome (25 mg ml$^{-1}$) (FIG. 3). The enhanced quadruplet decoding was further confirmed by in vitro CAT assays[32] (FIG. 5), which also confirm that resistance is linear with chloramphenicol acetyl transferase activity (not shown). To ascertain if the enhanced activity of ribo-X on quadruplet codons is at the expense of triplet decoding we compared the chloramphenicol resistance conferred by ribo-X to that conferred by the progenitor O-ribosome on cells containing O-cat. We find no difference in activity; both ribosomes support growth to 500 mg ml$^{-1}$, indicating that ribo-X is efficient at reading triplet codons.

Ribo-X Shows Specificity for Fourth Base Interaction & Preferentially Decodes Quadruplet over Triplet Codons with Extended Anticodon tRNAs We investigated the specificity of ribo-X for Watson-Crick base pairing in the fourth position of the codon-anticodon interaction by measuring the chloramphenicol acetyl transferase activity of ribo-X with O-cat (UAGN103, UAGN146)/tRNA$^{ser2}$ (UCUA). We find that ribo-X shows a selectivity of more than ten-fold for the cognate A:U pair, over any other base-pair at the fourth position. (FIG. 6) consistent with previous reports for the natural ribosome[33].

To investigate whether ribo-X preferentially decodes a quadruplet codon over a triplet codon, when supplied with an extended anticodon tRNA, we compared the chloramphenicol resistance conferred by an O-cat gene in which codon 103 is UAG and codon 104 begins with an A (O-frame UAGA, FIG. 2) with that conferred by an O-cat gene containing an in-frame UAGA quadruplet codon at position 103. We find that ribo-X and tRNA$^{ser2}$ (UCUA) confer resistance to chloramphenicol up to 20 mg ml$^{-1}$ on the triplet codon reporter and up to 400 mg ml$^{-1}$ on the quadruplet codon reporter. These data suggest that less than 5% of the termination on quadruplet codons with ribo-X results from triplet decoding, and that with the extended anticodon tRNA, ribo-X prefers quadruplet over triplet decoding by approximately 10-fold.

Ribo-X Shows Increased Efficiency in Decoding Quadruplet Codons

To begin to explore the extent to which enhanced quadruplet decoding of UAGA and AGGA with ribo-X is portable to other extended anticodons, we first altered the anticodon of the tRNA to GCUA, CCUA, or ACUA and altered the codons at position 103 in the O-cat gene to their Watson-Crick complement (UAGC, UAGG, UAGU). Ribo-X shows an up to 8-fold increase in efficiency at decoding quadruplet codons with respect to the progenitor O-ribosome (FIG. 4). In addition we find that ribo-X enhances translational efficiency 2.5-fold with a CCCU reporter in the presence of a cognate extended anticodon tRNA.

Ribo-X Increases Amber Decoding and UAGN decoding by Decreasing Functional Interactions with Release Factor.

The decoding enhancement with UAGN codons is generally larger than that observed with AGGA and CCCU codons, and this prompted us to ask whether ribo-X enhances decoding of UAGN codons in part by decreasing its functional interaction with release factor 1 (RF1). The ribosome binds RF1 in response to amber codons in the ribosomal A site, and causes peptide chain termination[34]. RF1-mediated termination is therefore believed to compete with amber suppressor tRNA mediated peptide chain elongation in response to an amber codon in the ribosomal A-site. Ribosomes that do not functionally interact with RF1 but are still able to perform protein synthesis and function with NCUA tRNAs would be more efficient than un-evolved ribosomes at decoding UAGN codons. If the enhanced, activity of ribo-X on UAGN codons were due in part to a decreased functional interaction with RF1 then ribo-X should be more efficient at decoding the amber stop codon (UAG) with an amber suppressor tRNA. Indeed we find that when we contract the anticodon from UCUA to CUA, the resulting suppressor tRNA is 8 times more efficient at decoding an amber codon at position 103 in O-cat with ribo-X than with the progenitor O-ribosome (FIG. 4). This suggests that a major mechanism by which ribo-X increases its efficiency on UAGN codons is by decreasing its functional interaction with release factor, and provides evidence for a functional interaction between the 530 loop of the ribosome and RF1 that is consistent with, but not predicted by, the 5.9 Å X-ray structure of RF1 bound to the ribosome[35]. In contrast to temperature sensitive mutants in the essential RF1 protein, mutants in the cellular ribosome that allow transient increases in suppression across all mRNAs at the expense of cellular viability[33,36,37], or mutants in rRNA that cause misreading of amber codons in the absence of a cognate tRNA[38] the effect of ribo-X is localized to the population of orthogonal mRNAs that it decodes. Ribo-X increases tRNA dependent amber suppression in a target gene without increasing read through of amber codons in natural cellular mRNAs and therefore does not perturb decoding of the natural transcriptome.

Ribo-X is Optimized for the 32-38 Pair in Extended Anticodon tRNAs

While we observe a strong effect on UAGN and UAG decoding we also see improvements, albeit more modest, in the efficiency of decoding the quadruplet codons AGGA and CCCU codons by cognate extended anticodon tRNAs (FIG. 4). In these cases release factors are not believed to compete with the tRNA for A-site binding, suggesting that the decreased functional interaction with RF1 cannot account for all the properties of ribo-X. We therefore looked for features within the tRNA structure which ribo-X might be optimized to recognize.

The extended anticodon tRNAs used in this study have purines at position 32 in the anticodon loop and phylogenetically unusual combinations of nucleotides at positions 32 and 38[39]. Uhlenbeck and coworkers have shown, in the context of triplet decoding, that natural variation in the identity of the 32-38 pair can influence the affinity of tRNAs for the ribosomal A-site[40]. The A site of ribo-X may have optimized affinity for expanded anticodon tRNAs with unusual nucleotides at position 32 and 38 while maintaining close to optimal affinity for natural tRNAs. Consistent with this view, we find that conversion of the 32-38 pair in the AGGA tRNA from A32C38 to C32A38, as found in tRNA$^{ser2}$ produces an extended anticodon tRNA read equally poorly by the progenitor O-ribosomes and by ribo-X (FIG. 4).

We have demonstrated the first example of synthetic evolution of ribosome function in living cells. We have shown that orthogonal ribosomes can be evolved to more efficiently decode a range of extended codons using tRNAs with extended anticodon loops. The evolved orthogonal ribosome, ribo-X, preferentially reads quadruplet codons with extended anticodon tRNAs and can show specificity for Watson-Crick base pairs at the fourth position of the codon-anticodon interaction. Ribo-X also improves amber suppression by amber suppressor tRNAs. Finally we have provided experimental support for a model which explains the mode of action of ribo-X, and implicates the 530 loop, in the ribosome decoding centre, in functional interactions with RF1.

The observation that ribo-X can improve the efficiency with which full length proteins are synthesized from orthogonal mRNAs containing amber codons has technological significance. Almost all current methods of introducing unnatural amino acids into proteins in vivo rely on amber suppression, and produce a large fraction of truncated protein[41-44], as a result of release factor mediated peptide chain termination. Release factor mediated protein truncation reduces protein yield and, for in vivo studies using unnatural amino acids to probe cellular function[45, 46], truncated proteins can have unforeseen functional and phenotypic effects that perturb precisely the system under investigation. Ribo-X should facilitate in vivo studies with unnatural amino acids and may also allow improvements in total protein yield for expression systems that exploit incorporation of unnatural amino acids in response to the amber codon. Importantly since ribo-X's primary mode of action on UAG codons is decreasing release factor binding it will exert its enhancement of UAG decoding for the wide range of amber suppressor tRNAs used for unnatural amino acid incorporation in E. coli.

By improving the quadruplet decoding of the orthogonal ribosome we have diverged the decoding properties of the orthogonal ribosome from those of the cellular ribosome such that the same insertion signal is read with a different efficiency on cellular and orthogonal mRNAs within the same cell. Since the meaning of codons on any mRNA is set by the translational machinery that decodes that mRNA, it may be possible to use extensions of our approach to bypass the "frozen accident" of the existing genetic code[47] and write quadruplet codes or other genetic codes on orthogonal mRNAs, using tRNAs that are poor substrates for the cellular ribosome but are efficiently decoded by evolved orthogonal ribosomes. Such parallel and independent codes (orthogonal genetic codes) would expand the information storage capacity of the cell and might be used to extend in vitro computation[48, 49] to living cells. Moreover orthogonal codes might be used to encode the biosynthesis of unnatural polymers and to create insulated genetic codes for encoding the components of synthetic genetic circuits in a form unreadable by, and therefore not functionally transmissible to, natural biological entities.

Example 3

Evolved Orthogonal Ribosomes with Enhanced Efficiency

Design of a Ribosome Decoding Centre Library

The A-site of the ribosome is the gateway to the tRNA translocation corridor composed of the A, P and E sites[28-30]. In response to an amber codon in the A-site of the ribosome RF-1 can bind to the A-site and compete with decoding of amber suppressor tRNAs. We reasoned that combinations of mutations in 16S rRNA, which forms the A-site of the ribosome, might yield a variant A-site that allows amber suppressor tRNAs to compete more effectively with RF-1 for A-site binding, and thus favour amber suppression and elongation over polypeptide chain termination.

Figure 8:
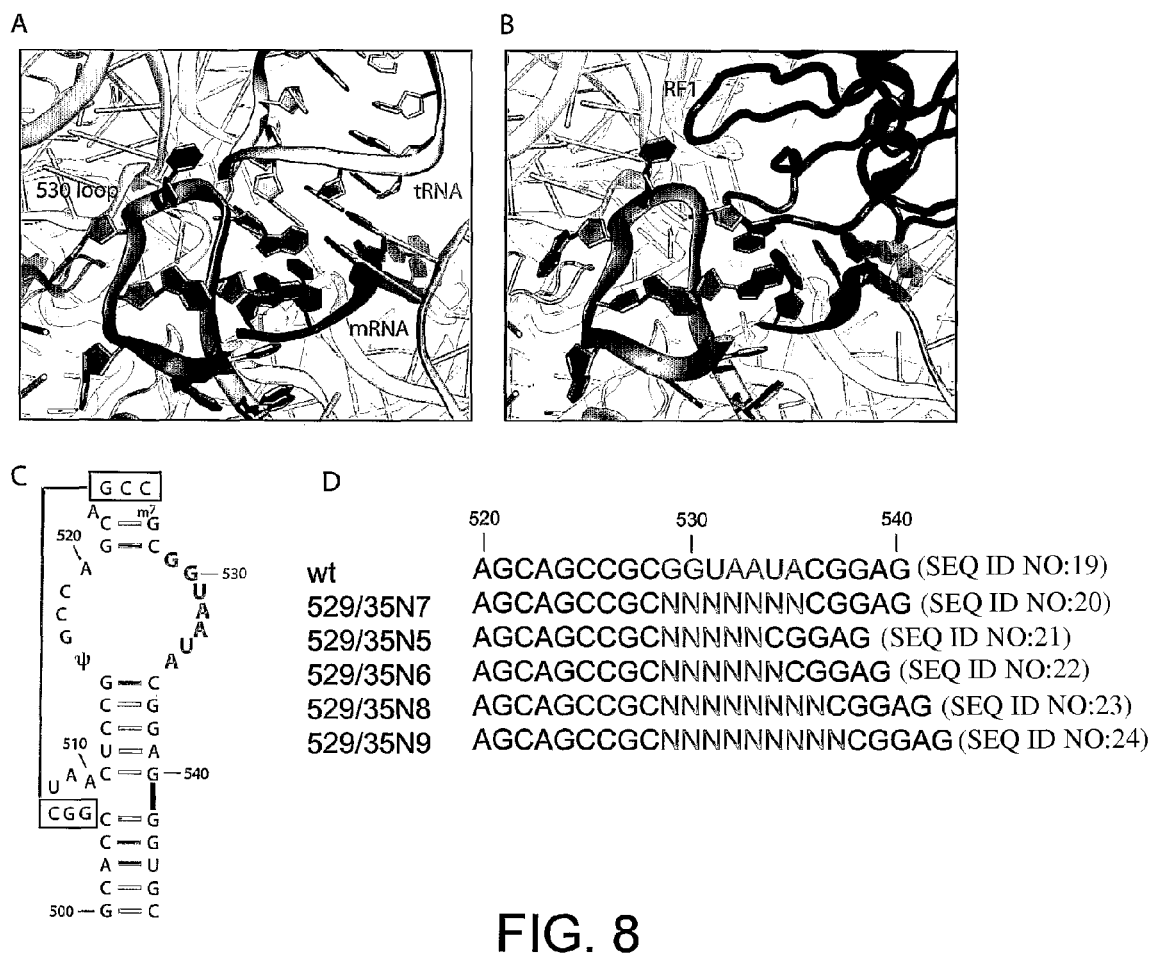
FIG. 8. Design of ribosome decoding libraries. A. Structure of a tRNA anticodon stem loop (yellow) bound to mRNA (purple) in the A site of the ribosome (green). The 530 loop is shown in orange. B. Structural model of RF-1 (blue) bound in the A-site of the ribosome C. Secondary structure of the 530 loop. The boxed sequences form a pseudo knot, ψ is pseudouridine and m$^7$G is 7-methyl guanosine. D. The sequence of ribosome decoding libraries. 3D structure figures were created using Pymol v0.99 and PDB IDs 1IBM and 2B64.

To design an A-site library (FIG. 8) we examined the structures of tRNAs or RF-1 bound to the ribosomal A-site[29-32]. These structures show that the 530 loop in 16S rRNA is proximal to both substrates (FIG. 8). We reasoned that combinations of mutations in the 530 loop might maintain tRNA binding, but decrease functional interaction with RF-1 in the presence of a UAG codon. We therefore randomized seven nucleotides (529-535) in the 530 loop to all combinations of nucleotides to create an N7 library. Moreover, we created longer and shorter 530 loop sequence libraries (N5, N6, N8, and N9 (FIG. 8)) to expand the functional space sampled. All libraries were more than 99% complete (Supplementary Table 1).

Selection of Evolved Decoding in Orthogonal Ribosomes

To create a selection system for orthogonal ribosomes that more efficiently read amber codons, we required a reporter of orthogonal ribosome activity that contains selector codons. We decided to work initially with a UAGA containing reporter and tRNA$^{ser2}$ (UCUA) (FIG. 14), which is aminoacylated by seryl-tRNA synthetase[33], rather than a simple UAG suppressor, because it allows selection for improved ribosome activity over a larger dynamic range. Cells containing O-cat (UAGA103, UAGA146)/tRNA$^{ser2}$ (UCUA) and the O-ribosome had an IC$_{50}$ on chloramphenicol of 25 µg ml$^{-1}$. For comparison, the O-cat reporter devoid of UAGA codons supports growth on 500 µg ml$^{-1}$ of chloramphenicol in the presence of the O-ribosome.

Figure 9:
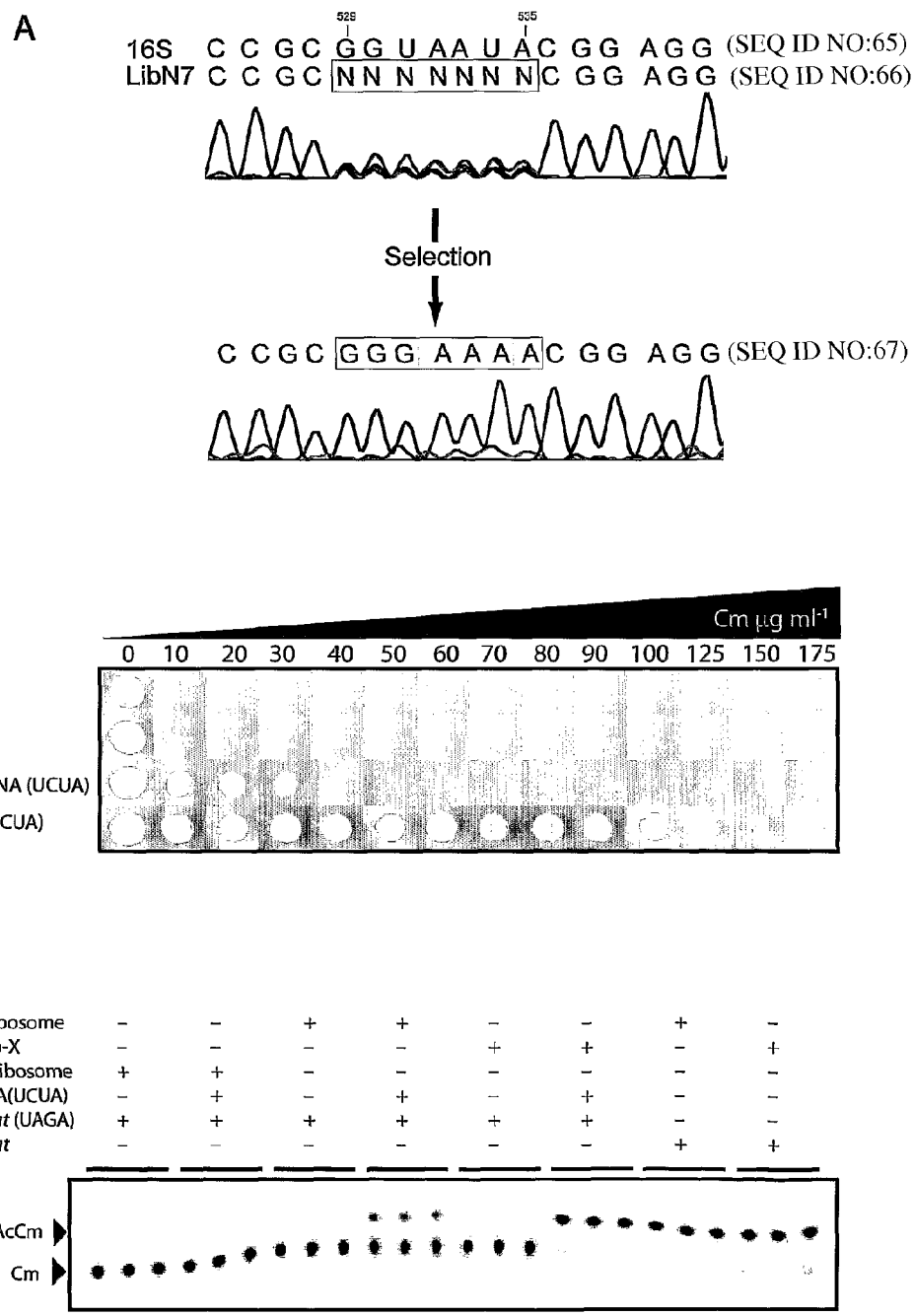
FIG. 9. Selection and phenotypic characterization of ribo-X. A. The selection of ribosomes that decode UAGA and UAG codons, using cognate tRNAs derived from tRNA$^{ser2}$. The top sequence trace shows the 16S rDNA before selection, while the lower traces show the convergence of the pool (sequencing from all colonies surviving a selection on chloramphenicol plates). B. The ribo-X, tRNA$^{ser2}$ (UCUA) dependent enhancement in decoding UAGA codons in the O-cat (UAGA103, UAGA146) gene measured by survival on chloramphenicol. C. As in B, but measuring CAT activity directly. Thin-layer chromatography (TLC) showing the acetylation of chloramphenicol (Cm) to acetylated chloramphenicol (AcCm) by CAT produced from either O-cat or O-cat (UAGA103, UAGA146).
Figures 14, 15:
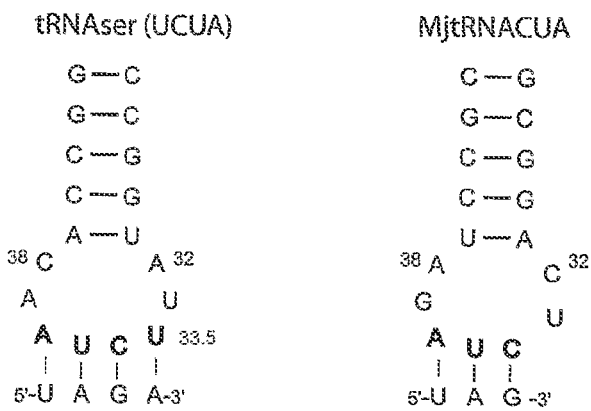
FIG. 14 shows the anticodon stem loops of the tRNAs used.
FIG. 15 shows the context of UAGA and UAG selector codons in cat reporter genes.

To select mutant ribosomes that more efficiently decode the UAGA codon we combined each orthogonal ribosome library with O-cat (UAGA103, UAGA146)/tRNA$^{ser2}$ (UCUA) (in which cat containing UAGA codons is translated from an orthogonal ribosome binding site, FIG. 15) and challenged the cells to grow on chloramphenicol concentrations at which the O-ribosome does not support growth. No clones containing insertions or deletions survived for libraries N5, N6, N8 and N9, suggesting that the 530 loop is intolerant to longer or shorter sequences of any composition. However, clones from the N7 library did survive on 100 μg ml$^{-1}$ chloramphenicol. All ten clones sequenced from the N7 selection were identical, and contained the mutations U531G and U534A in 16S rRNA (FIG. 9). The U531G mutation is present in only two sequenced vertebrate mitochondrial rRNAs while the U534A mutation is present in 0.2% of bacterial rRNAs. No sequenced natural ribosome contains this combination of mutations[34]. Because it remained a formal possibility that more efficient ribosomes for UAG decoding existed in the libraries but were not captured by the UAGA selection we repeated the selection with reporters containing the UAG codon and an amber suppressor derived from tRNA$^{ser2}$ (FIG. 14). We found that the same sequence was uniquely selected. We therefore decided to characterize the U531G, U534A mutant ribosome, which we refer to as ribo-X, in more detail.

Ribo-X Enhances tRNA Dependent UAGA Decoding

To measure the extent to which ribo-X enhances tRNA$^{ser2}$ (UCUA) dependent decoding of the UAGA codon, we compared the chloramphenicol resistance of cells containing O-cat (UAGA103, UAGA146)/tRNA$^{ser2}$ (UCUA) and either ribo-X or the progenitor O-ribosome (FIG. 9). Ribo-X containing cells survive on concentrations of chloramphenicol five times higher than cells containing the progenitor O-ribosome. The enhanced, tRNA$^{ser2}$ (UCUA) dependent, quadruplet decoding was further confirmed by in vitro chloramphenicol acetyl transferase (CAT) assays[35] (FIG. 9). Similar ribo-X mediated enhancements were observed using tRNA$^{ser2}$ (CUA) and a cognate O-cat reporter. The chloramphenicol resistance conferred on cells by ribo-X and O-cat and the progenitor O-ribosome and O-cat is identical (500 μg ml$^{-1}$), indicating that ribo-X is efficient and processive in translation of sense codons.

Ribo-X and Natural Ribosomes have Comparable Fidelity

To demonstrate that ribo-X synthesizes proteins with a fidelity comparable to the natural ribosome, we compared the mass spectra, and amino acid mis-incorporation frequency of proteins synthesized by wild-type ribosomes, the progenitor orthogonal ribosome and ribo-X.

Figure 10:
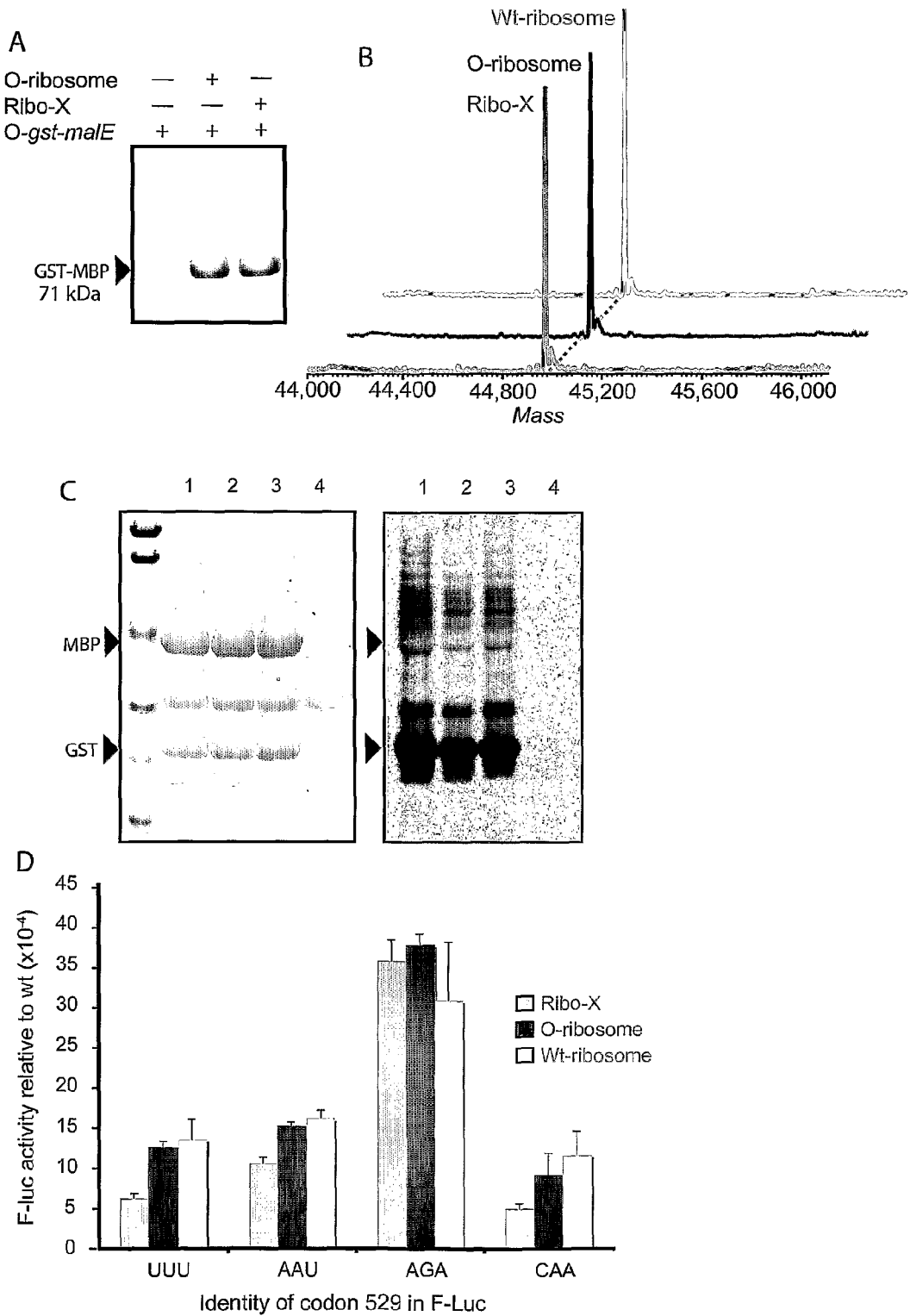
FIG. 10. The translational fidelity of ribo-X is comparable to that of the natural ribosome. A. Translation from O-gst-malE is dependent on ribo-X or the O-ribosome. B. Ribo-X synthesizes proteins of identical composition to those synthesized by the wild-type ribosome, as judged by electrospray ionization mass spectrometry. The electrospray ionisation spectra of MBP synthesized by ribo-X, the progenitor O-ribosome or the wild-type ribosome is shown. Each ribosome was used to synthesize the GST-MBP protein, which was purified on glutathione sepharose and subject to thrombin cleavage at a site in the linker (FIG. 16). The resulting pairs of fragments have identical electrospray ionization spectra (Found: O-ribosome 44984 Da, ribo-X 44984 Da, wt ribosome 44984 Da, expected 44981 Da). C. The translational error frequency measured by $^{35}$S-cysteine mis-incorporation is indistinguishable for ribo-X and the natural ribosome. GST-MBP was synthesized by each ribosome in the presence of $^{35}$S-cysteine, purified on glutathione sepharose and digested with thrombin. The left panel shows a coomassie stain of the thrombin digest. The un-annotated bands result primarily from the thrombin preparation. The right panel shows $^{35}$S labelling of proteins in a similar gel, imaged using a Storm Phoshoimager, a coomassie stain of the $^{35}$S gel is shown in FIG. 19. Lanes 1-3 show thrombin cleavage reactions of purified protein derived from cells containing pSC101*-ribo-X & pO-gst-malE, pSC101*-O-ribosome and pO-gst-malE, and pSC101*-BD and pgst-malE. Lane 4 is a negative control in which cells lacking a gst-malE gene fusion were treated identically to the other samples. The size markers are pre-stained standards (Bio-Rad 161-0305) D. The translational fidelity of ribo-X is comparable to that of the natural ribosome as measured by a dual luciferase assay. In this system a C-terminal firefly luciferase is mutated at codon K529(AAA), which codes for an essential lysine residue. The extent to which the mutant codon is misread by tRNA$^{Lys}$ (UUU) is determined by comparing the firefly luciferase activity resulting from the expression of the mutant gene to the wild-type firefly luciferase, and normalizing any variability in expression using the activity of the co-translated N-terminal Renilla luciferase. Previous work has demonstrated that measured firefly luciferase activities in this system result primarily from the synthesis of a small amount of protein that mis-incorporates lysine in response to the mutant codon, rather than a low activity resulting from the more abundant protein containing encoded mutations[37]. In experiments examining the fidelity of ribo-X, lysate from cells containing pSC101*-ribo-X and pO-DLR and its codon 529 variants were assayed. Control experiments used lysates from cells containing pSC101*-O-ribosome and pO-DLR and its codon 529 variants or pwt-DLR and its variants. Assays on pO-DLR in the presence and absence of the orthogonal ribosome or ribo-X indicate that greater than 98% of translation on pO-DLR is derived from ribo-X or the orthogonal ribosome (FIG. 17), confirming that the fidelity measurements on pO-DLR reflect the activity of ribo-X.
Figures 16, 17:
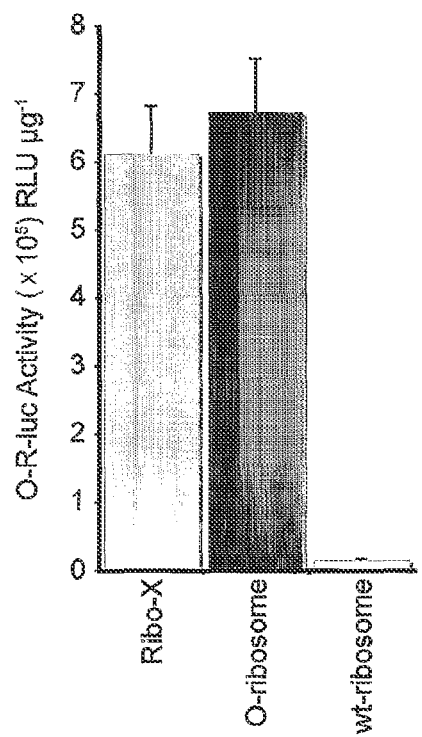
FIG. 16 shows the linker region of the gst-malE expression construct. The codons mutated in gst(UAG)$_n$malE constructs are indicated. The thrombin cleavage site in GST-MBP is indicated.
FIG. 17 shows the ribosome dependence of O-DLR derived renilla luciferase (O-R-luc) activity. O-ribosomes or ribo-X lead to a 40-45 fold activation, indicating that in the presence of O-ribosomes greater than 97% of the luciferase fusion is produced by O-ribosomes. The error bars indicate the standard error.

Expression of O-gst-malE (a genetic fusion between the genes encoding glutathione-S-transferase (GST) and maltose binding protein (MBP) driven by an orthogonal ribosome binding site) in the presence of ribo-X or the progenitor O-ribosome produced GST-MBP with a purified yield of 30-40 mg l$^{-1}$, comparable to the yield of GST-MBP produced from a gst-malE fusion by wild-type ribosomes. As expected, no GST-MBP can be purified from O-gst-malE in the absence of orthogonal ribosomes (FIG. 10a). Thrombin cleavage of GST-MBP, at a site between GST and MBP in the protein fusion (FIG. 16), produced two proteins that were amenable to mass determination by electrospray ionization mass-spectrometry. Proteins produced from each ribosome had the same mass (FIG. 10b). To explicitly compare the translational fidelity of ribo-X to that of progenitor ribosomes, we measured the frequency of $^{35}$S-cysteine mis-incorporation[36] into MBP, which contains no cysteine codons (FIG. 10c). The error frequency per codon translated by ribo-X was less than 1×10$^{-3}$. Control experiments with the progenitor orthogonal ribosome and the wild-type ribosome allowed us to put the same limit on their error frequency. This limit compares well with a previous measurement for amino acid mis-incorporation frequency, as measured by $^{35}$S-cysteine mis-incorporation[36], of 4×10$^{-3}$ errors per codon. To further probe the translational fidelity of ribo-X with respect to defined perturbations in the codon-anticodon interaction, we took advantage of a dual luciferase reporter system (DLR) that has previously been used to measure the fidelity of natural and error-prone ribosomes in decoding near-cognate and non-cognate codons[37]. We created a DLR with an orthogonal ribosome-binding site (O-DLR), and demonstrated that its translation is dependent on the presence of a cognate orthogonal ribosome (FIG. 17). We translated O-DLR variants, for which K529(AAA) was mutated at each position of the codon-anticodon interaction (FIG. 10d), using ribo-X or the progenitor orthogonal ribosome, and compared the resulting luciferase activities as a measure of translational mis-reading. We find that the fidelity of ribo-X is at least as good as that measured for the progenitor orthogonal ribosome and the natural ribosome across all four codon-anticodon interactions tested.

Overall, the mass spectra, $^{35}$S mis-incorporation assay and dual luciferase assays demonstrate that ribo-X has a translational fidelity comparable to that of the natural ribosome.

Increased Efficiency Unnatural Amino Acid Incorporation

To demonstrate the substantial increase in efficiency of site-specific unnatural amino acid incorporation with ribo-X, we chose to work with the photocrosslinking amino acid p-benzoyl-L-phenylalanine (Bpa)[38]. This amino acid has been added to the genetic code of E. coli, yeast and mammalian cells and used extensively to map the topology of protein-protein interactions in vitro and in vivo[5, 20, 39-42].

Figure 11:
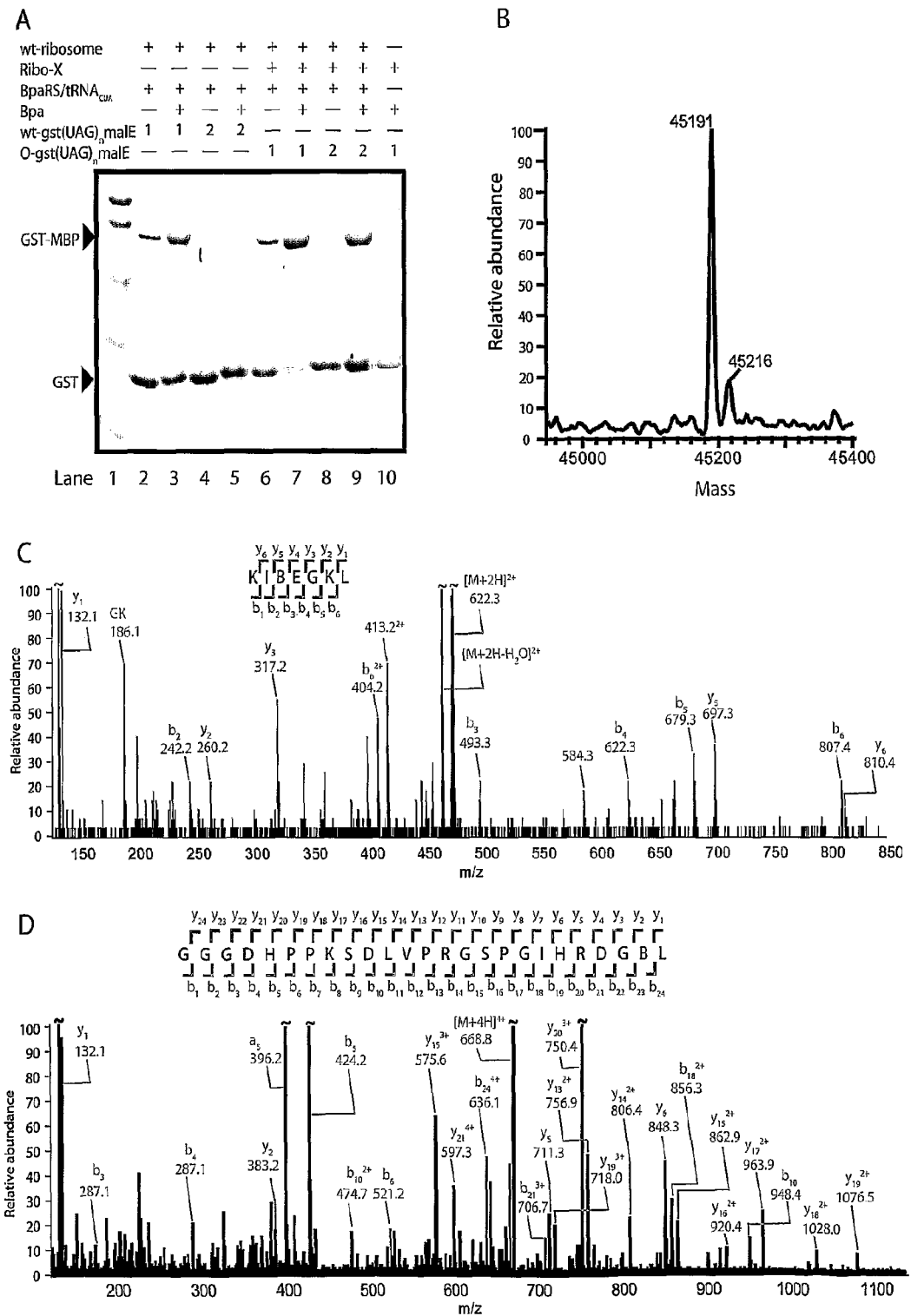
FIG. 11. A. Ribo-X enhances the efficiency of BpaRS/tRNA$_{CUA}$ dependent unnatural amino acid incorporation in response to single and double UAG codons. In each lane an equal volume of protein purified from glutathione sepharose under identical conditions is loaded. Ribo-X is produced from pSC101*-ribo-X derived rRNA. Bpa is p-benzoyl-L-phenylalanine. BpaRS is p-benzoyl-L-phenylalanyl-tRNA synthetase. BpaRS/tRNA$_{CUA}$ are produced from pSUPBpa[23] that contains six copies of MjtRNA$_{CUA}$ and is the most efficient unnatural amino incorporation vector reported to date. (UAG)$_n$ describes the number of stop codons (n) between gst and malE in O-gst(UAG)$_n$malE or gst(UAG)$_n$malE. Lane 10 is from a different gel. The markers are as described in FIG. 9. B. The mass of protein expressed from O-gst(UAG)$_2$malE by ribo-X is as expected for the incorporation of 2 Bpas. Purified full-length protein was cleaved with thrombin to produce an MBP fragment amenable to accurate mass determination. The found mass (45191) is identical to the expected mass for incorporation of two Bpas into MBP (45191.6). The small peak at 45216 Da is the Na$^+$ adduct. C & D. MS/MS fragmentation of chymotryptic peptides derived from GST-MBP synthesized by ribo-X and incorporating 2 Bpas. The spectra confirm Bpa incorporation at both the expected sites. The fragmentation sites for each fragment ion are illustrated above the spectra. B denotes Bpa.
Figure 18:
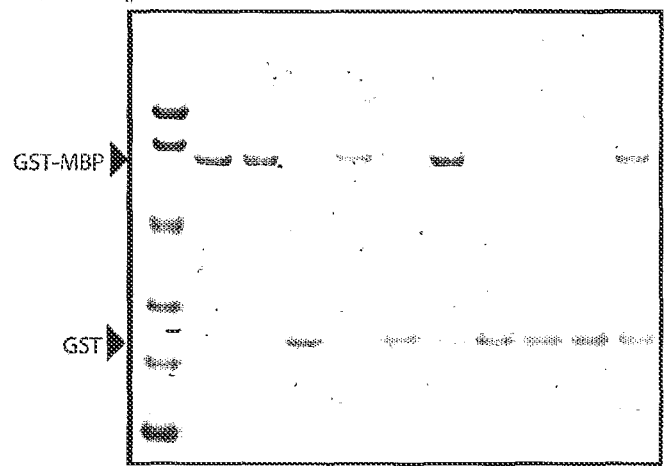
FIG. 18 shows the Ribo-X mediated enhanced unnatural amino acid incorporation efficiency is robust in minimal medium. Experiments were performed as described for FIG. 11A, except that minimal medium was used for expression. Similar results were observed when the efficiency of the progenitor ribosome was compared to Ribo-X. Molecular weight markers are as described in FIG. 10.
Figure 19:
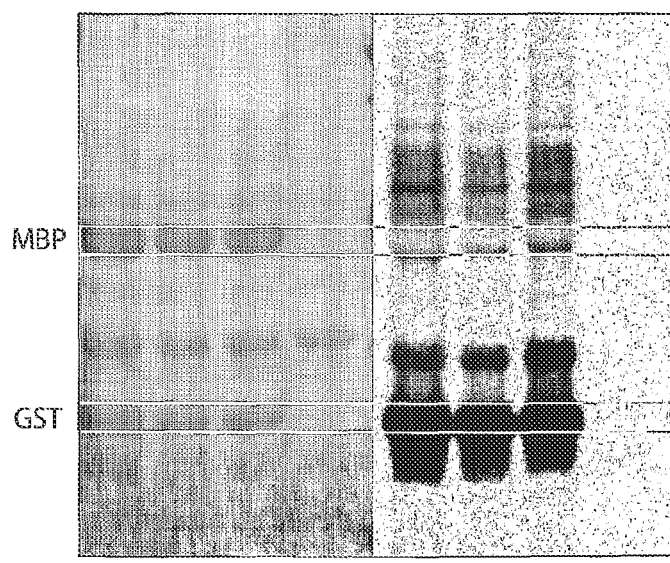
FIG. 19 shows 35S misincorporation in GST-MBP. The coomassie gel from which the 35S data in FIG. 10 was acquired and the corresponding 35S image are shown side-by-side. The alignment of the bands is indicated by the bounding boxes. The lanes are arranged identically to those in FIG. 10c.

We expressed gst(UAG)malE in the presence of a p-benzoyl-L-phenylalanyl-tRNA synthetase/tRNA$_{CUA}$ (BpaRS/tRNA$_{CUA}$) pair[39] (evolved from the MjTyrRS/tRNA$_{CUA}$ pair), Bpa and wild-type ribosomes (FIG. 11a). As expected this produced GST-MBP, incorporating Bpa, with low efficiency (24%). However when we synthesized GST-MBP containing Bpa from O-gst(UAG)malE using the BpaRS/tRNA$_{CUA}$ pair, Bpa, and ribo-X, the efficiency increased to 62%. As expected, based on the previously reported specificity of BpaRS, full-length protein synthesis is Bpa dependent[39]. In our experiments, performed in Luria Bertani (LB) medium as previously described[23], we see a small amount of full-length protein synthesis that is BpaRS and tRNA$_{CUA}$ dependent, but not amino acid dependent (compare FIG. 11a, lanes 2 and 6 and 10). This effect is minimized in minimal medium, where the total yields of overexpressed proteins are also approximately five times lower (FIG. 18). In the presence of Bpa, the aminoacylation of natural amino acids onto tRNA$_{CUA}$ by non-cognate aminoacyl-tRNA synthetases observed in rich media is out-competed, and incorporation of Bpa is quantitative[23] (FIG. 11b, c, d). Mass spectrometry shows that BpaRS expression from pSupBpa does not lead to detectable levels of unnatural amino acid incorporation in response to sense codons (via misacylation of endogenous tRNAs), as expected from the observation that MjTyrRS does not aminoacylate any E. coli tRNAs with tyrosine, even in the absence of competing endogenous aminoacyl-tRNA synthetase enzymes[43]. In the absence of a functional aminoacyl-tRNA synthetase/tRNA$_{CUA}$ pair ribo-X terminates translation on the amber codon, and no full-length GST-MBP fusion is purified (FIG. 11a, lane 10). Similarly, ribo-X does not measurably enhance read-through of a UAA or UGA codons.

The ribo-X mediated enhancement of efficiency was even more dramatic for a gene containing two amber stop codons (FIG. 11a): wild-type ribosomes produced GST-MBP containing two Bpas from gst(UAG)$_2$malE with an efficiency of less than 1%, while ribo-X produced GST-MBP containing two Bpas with an efficiency at least twenty-fold higher (22%) from O-gst(UAG)$_2$malE. Extrapolation of the single UAG efficiencies to two sites predicts efficiencies of 38% and 6% for ribo-X and the wild-type ribosome respectively. Comparison of the ratio of predicted to observed efficiencies for each ribosome suggests that ribo-X may be more robust than the wild-type ribosome to context effects which decrease the efficiency of UAG suppression[44] Electrospray ionization mass spectrometry of MBP produced by ribo-X in the presence of the BpaRS/tRNA$_{CUA}$ pair and Bpa confirmed the incorporation of 2 Bpas; no peaks were detected corresponding to the incorporation of natural amino acids (FIG. 11b). The sites of Bpa incorporation were further confirmed by analysis of the MS/MS fragmentation series of the relevant chymotryptic peptides (FIGS. 11c & 11d). We observe that the ribo-X mediated improvement in efficiency for one and two amber codons is conserved in minimal medium (FIG. 18), demonstrating that the effect mediated by ribo-X is robust under different expression conditions. Overall, the protein expression data and mass spectrometry data clearly demonstrate that the modular combination of ribo-X, BpaRS/tRNA$_{CUA}$ and an orthogonal mRNA containing multiple UAG codons allows the site-specific incorporation of Bpa with high fidelity and efficiency at multiple sites in GST-MBP.

Materials and Methods to Example 3:

Construction of Ribosome Libraries and Reporters 16S rDNA libraries were constructed by enzymatic inverse PCR[25] on pRSF vectors containing a previously described O-rDNA (pRSF-O-rDNA)[48]. To create the UAGA reporter plasmid we introduced the amber derived UAGA codon at two sites in the chloramphenicol acetyl transferase (cat) gene (Ser103 and Ser146, an essential and conserved catalytic serine residue[49] that ensures the fidelity of incorporation, FIG. 15), downstream of an orthogonal ribosome-binding site, producing O-cat (UAGA103, UAGA146). This construct was created by multiple rounds of Quik Change mutagenesis (Stratagene) on an O-cat reporter derived from p21[25] by replacement of the cat-upp fusion with the cat gene alone. tRNA genes were introduced into the O-cat (UAGA103, UAGA146) plasmid at a unique Bst Z17I restriction site, via a cassette containing a 5' synthetic lpp promoter and a 3' rrnC transcriptional terminator, to create the vector O-cat (UAGA103, UAGA146)/tRNA(UCUA); the sequence of the extended anticodon is written 5' to 3'. UAG codon reporters and CUA anticodon tRNAs were derived by Quik Change mutagenesis from the UAGA or UCUA constructs. All final plasmids were confirmed by DNA sequencing. For a complete description of oligonucleotides used for vector construction see Supplementary Table 2.

Selection of Evolved O-Ribosomes

To select O-ribosomes with improved UAGA decoding, each pRSF-O-rDNA library was transformed by electroporation into GeneHog E. coli (Invitrogen) containing O-cat (UAGA103, UAGA146)/tRNA(UCUA). Transformed cells were recovered for 1 h in SOB medium containing 2% glucose and used to inoculate 200 ml of LB-GKT (LB medium with 2% glucose, 25 µg ml$^{-1}$ kanamycin and 12.5 µg ml$^{-1}$ tetracycline). After overnight growth (37° C., 250 r.p.m., 16 h), 2 mL of the cells were pelleted by centrifugation (3000 g), and washed three times with an equal volume of LB-KT (LB medium with 12.5 µg ml$^{-1}$ kanamycin and 6.25 µg ml$^{-1}$ tetracycline). The resuspended pellet was used to inoculate 18 ml of LB-KT, and the resulting culture incubated (37° C., 250 r.p.m. shaking, 90 min). To induce expression of plasmid encoded O-rRNA, 2 ml of the culture was added to 18 ml LB-IKT (LB medium with 1.1 mM isopropyl-D-thiogalactopyranoside (IPTG), 12.5 µg ml$^{-1}$ kanamycin and 6.25 µg ml$^{-1}$ tetracycline) and incubated for 4 h (37° C., 250 r.p.m.). Aliquots (250 µl optical density at 600 nm (OD$_{600}$)=1.5) were plated on LB-IKT agar (LB agar with 1 mM IPTG, 12.5 µg ml$^{-1}$ kanamycin and 6.25 µg ml$^{-1}$ tetracycline) supplemented with 50 µg ml$^{-1}$ chloramphenicol and incubated (37° C., 40 h).

Characterization of Evolved O-Ribosomes

To separate selected pRSF-O-rDNA plasmids from the O-cat (UAGA103, UAGA146)/tRNA$^{ser2}$ (UCUA) reporter plasmids, total plasmid DNA from selected clones was purified and digested with Not I restriction endonuclease, and transformed into DH10B E. coli. Individual transformants were replica plated onto kanamycin agar and tetracycline agar and plasmid separation of pRSF-O-rDNA from the reporter confirmed by restriction digest and agarose gel analysis.

To quantify the UAGA decoding activity of selected 16S rDNA clones, selected pRSF-O-rDNA plasmids were co-transformed with O-cat (UAGA103, UAGA146) or O-cat (UAGA103, UAGA146)/tRNA$^{ser2}$ (UCUA). Cells were recovered (SOB, 2% glucose, 1 h) and used to inoculate 10 mL of LB-GKT, which was incubated (16 h, 37° C., 250 r.p.m.). 1 ml of the resulting culture was used to inoculate 9 ml of LB-KT, which was incubated (90 min, 37° C., 250 r.p.m.). 1 ml of the LB-KT culture was used to inoculate 9 ml of LB-IKT medium, which was incubated (37° C., 250 r.p.m., 4 h). Individual clones were transferred to a 96-well block and arrayed, using a 96 well pin tool, onto LB-IKT agar plates containing chloramphenicol at concentrations from 0 to 250 µg ml$^{-1}$. The plates were incubated (37° C., 16 h). We performed analogous experiments for other tRNA codon pairs.

To extract soluble cell lysates for in vitro CAT assays, 1 ml of each induced LB-IKT culture was pelleted by centrifugation at 3,000 g. The cell pellets were washed three times with 500 µl Washing Buffer (40 mM Tris-HCl, 150 mM NaCl, 1 mM EDTA, pH 7.5) and once with 500 µl Lysis Buffer (250 mM Tris-HCl, pH 7.8). Cells were lysed in 200 µl Lysis Buffer by five cycles of flash-freezing in dry-ice/ethanol followed by rapid thawing in a 50° C. water-bath. Cell debris was removed from the lysate by centrifugation (12,000 g, 5 min) and the top 150 µl of supernatant frozen at −20° C. To assay CAT activity in the lysates, 10 µl of soluble cell extract was mixed with 2.5 µl of FAST CAT Green (deoxy) substrate (Invitrogen) and pre-incubated (37° C., 5 min). 2.5 µl of 9 mM acetyl-CoA (Sigma) was added, and the reaction incubated (37° C., 1 h). The reaction was stopped by the addition of ice-cold ethyl acetate (200 µl, vortex 20 s). The aqueous and organic phases were separated by centrifugation (12,000 g, 10 min) and the top 100 µl of the ethyl acetate layer collected. 1 µl of the collected solution was spotted onto a silica gel TLC plate (Merck) for thin-layer chromatography in chloroform:methanol (85:15 v/v). The fluorescence of the spatially resolved substrate and product was visualized and quantified using a phosphorimager (Storm 860, Amersham Biosciences) with excitation and emission wavelengths of 450 nm and 520 nm, respectively.

Construction of GST-MBP Protein Expression Vectors gst was amplified from pGEX-2T (GE Healthcare) with the primers: GAACTCGAGACAATTTTCATATCCCTC-CGCAAATGTCCCCTATACTAGGTTATTGGA AAAT-TAAG (SEQ ID NO:1) and GAAGAGGTACCCGTCAC-GATGAATTCCCGGGGATCCACGCGGAAC (SEQ ID NO:2), and digested with Xho I and Kpn I. malE was amplified from pMAL (NEB) with PCR primers GAAGGGTAC-CTCAAAATCGAAGAAGGTAAACTGGTAATC (SEQ ID NO:3) and CCAAAGCTTAGCTTGCCTGCAGGTC-GACTC (SEQ ID NO:4) and digested with Hind III and Kpn I. pO-gst-malE was generated from pGFPmut3.1 (Promega), by replacing $A^{191}T^{192}A^{193}$ in the vector with CTCGAG (Xho I site). This mutates the lac operator and renders expression of the downstream gene constitutively active. Gfp was excised from between the Hind III site and the newly introduced Xho I site, and the gst-malE fusion introduced with the same sites via a three-fragment ligation. The vector p gst-malE was created by changing the orthogonal ribosome binding site to a single wildtype ribosome binding site with the enzymatic inverse PCR primers: GTAGGTCTCGGATCCCCGGG-TACCTAGAATTAAAGAGGAGAAATTAAGCATGTCC CCTATACTAGGTTATTG (SEQ ID NO:5) and GTAG-GTCTCGGATCCTCTAGAGTCGACCTG-CAGGAATGCAAGCTTGGCGTAACTC GAGCCGCT-CACAATTCCACAC (SEQ ID NO:6). To create vectors containing a single amber codon between gst and malE (pgst (UAG)malE and pO-gst(UAG)malE) the Tyr codon, TAC, in the linker between gst and malE was changed to TAG by Quik Change mutagenesis (Stratagene), using the primers GAAT-TCATCGTGACGGGTAGCTCAAAATCGAA-GAAGGTAAACTGGTAATCTG (SEQ ID NO:7) and CTTCGATTTTGAGCTACCCGTCACGAT-GAATTCCCGGGGATCCACGCGGAAC (SEQ ID NO:8). For double UAG mutants we additionally mutated the fourth codon in malE from GAA to TAG by Quik Change, with the primers CTCAAAATCTAGGAAGGTAAACTGG-TAATCTGGATTAACGGCGATAAAG (SEQ ID NO:9) and CAGTTTACCTTCCTAGATTTTGAGCTAC-CCGTCACGATG (SEQ ID NO:10) to create the vectors pgst(UAG)^malE and pO-gst(UAG) 2malE.

Construction of P1P2 Ribosomes for Protein Expression

The kanamycin resistance gene and the SC101* origin of plasmid pZS*24-MCS1[50] were amplified using the following primers: KanSC101fw, ACT GGA TCC TGC TAG AGG CAT CAA ATA AAA C (SEQ ID NO:11), and KanSC101rv, AGT ACC GGT TAG ACG TCG AAA TTG CCA GC (SEQ ID NO:12). The resulting PCR product was digested with Bam HI and Age I. The rrnB operon, including the P1P2 promoter and rrnC terminator, was excised from plasmid pTrc P1P2 rrnB by digestion with NgoM IV and Bam HI, and the amplified SC101* fragment and P1P2rrnB fragment were ligated to create plasmid pSC101*-BD. The Xho I/Xba I fragment of this plasmid was replaced with a corresponding fragment from pTrcRSF-O-rRNA or pTrcRSF-ribo-X, yielding pSC101*-O-ribosome and pSC101*-ribo-X, respectively.

Expression and Purification of GST-MBP Fusions

E. coli containing the appropriate plasmid combinations were pelleted (3000 g, 10 min) from 50 ml, overnight cultures, resuspended in 1 ml Lysis buffer (Phosphate buffered saline (PBS) supplemented with 1× protease inhibitor cocktail (Roche), 1 mM PMSF and 1 mg ml$^{-1}$ lysozyme (Sigma)), and incubated (15 min, 37° C., 1000 r.p.m.). Cells were chilled on ice before lysis by sonication (30 s, 30 W). The lysate was clarified by centrifugation (6 min, 25000 g, 2° C.). GST containing proteins from the lysate (875 µg, 400 µl) were bound in batch (1 h, 4° C.) to 50 µl of Glutathione sepharose beads (GE Healthcare). Beads were washed 3 times with 1 ml PBS, before elution by heating for 10 min at 80° C. in 60 µl 1×SDS gel-loading buffer. All samples were analysed on 4-20% Tris-Glycine gels (Invitrogen).

The densities of the bands for GST-MBP and GST were quantified from Coomassie stained gels with NIH image 1.63. We divided the background-corrected values by the molecular mass of the corresponding proteins (GST-MBP, 71 kDa and GST, 27 kDa) and used these values to calculate the percentage of amber codon suppression, by dividing the amount of GST-MBP by total amount of protein.

$^{35}$S-Cysteine Mis-Incorporation

GeneHog E. coli containing either pO-gst-malE and pSC101*-O-ribosome, pO-gst-malE and pSC101*-ribo-X or pgst-malE were resuspended in LB media (supplemented with $^{35}$S-cysteine (1000 Ci mmol$^{-1}$) to a final concentration of 3 nM, 750 µM methionine, 25 µg ml$^{-1}$ ampicillin and 12.5 µg ml$^{-1}$ kanamycin) to an $OD_{600}$ of 0.1, and cells were incubated (3.5 h, 37° C., 250 r.p.m.). 10 mL of the resulting culture was pelleted (5000 g, 5 min), washed twice (1 mL PBS per wash), resuspended in 1 mL PBS containing 1% Triton-X, and lysed on ice by pipetting up and down. The clarified cell extract was bound to 100 µL of glutathione sepharose beads (1 h, 4° C.) and the beads were pelleted (5000 g, 10 s) and washed twice in 1 mL PBS. The beads were added to 10 mL polypropylene column (Biorad) and washed (30 mL of PBS; 10 mL 0.5M NaCl, 0.5×PBS; 30 mL PBS) before elution in 1 mL of PBS supplemented with 10 mM glutathione. Purified GST-MBP was digested with 12.5 units of thrombin, to yield a GST fragment and an MBP fragment. The reaction was loaded onto an SDS-PAGE gel to resolve the GST, MBP and thrombin, and stained with GelCode blue (Invitrogen). The $^{35}$S activity in the GST and MBP protein bands were quantified by densitometry, using a Storm Phosphoimager (Molecular Dynamics) and ImageQuant (GE Healthcare) and by scintillation counting of excised bands. The error frequency per codon for each ribosome examined was determined as follows: GST contains 4 cysteine codons, so the number of counts per second (cps) resulting from GST divided by four gives A, the cps per quantitative incorporation of cysteine. MBP contains no cysteine codons, but mis-incorporation at non-cysteine codons gives B cps. Since GST and MBP are present in equimolar amounts, (A/B)×410, where 410 is the number of amino acids, in the MBP containing thrombin cleavage fragment, gives the number of amino acids translated for one cysteine mis-incorporation C. Assuming the mis-incorporation frequency for all 20 amino acids is the same as that for cysteine the number of codons translated per mis-incorporation is C/20, and the error frequency per codon is given by $(C/20)^{-1}$.

Dual Luciferase Assays pO-DLR contains a genetic fusion between a 5' Renilla Luciferase (R-luc) and a 3' Firefly Luciferase (F-luc) on an orthogonal ribosome binding site. To create pO-DLR the R-luc open reading frame from the plasmid pGL4.70[hRluc] (Promega) was amplified by PCR using the primers GAACTCGAGGGCGCGGCTTTCATATC-CCTCCGCAAATGGCCTCCAAGGTGTACGA CCCCGAGCAACGCAAACGCATG (SEQ ID NO:13) and GCTAGATCTCCTAGGGGCCCCCGTC-GAGATTTGCTCGTTCTTCAGCACGCGCTCC ACGAAGCTC (SEQ ID NO:14). The PCR product was digested with Xho I and Bgl II. The F-luc ORF was amplified with primer pair AGGAGATCTAGCGCTGGATC-CCCCGGGGAGCTCATCGAAGATGCCAAAAACATTA AGAAGGGCCCAG (SEQ ID NO:15) and GACAAGCTTA-CACGGCGATCTTGCCGCCCTTCTTG (SEQ ID NO:16) and digested with Bgl II and Hind III. The gst-malE gene fusion was excised from pO-gst-malE by Xho I and Hind III digestion and pO-DLR created by a triple ligation of the released vector backbone with the digested F-luc PCR product and the digested R-luc PCR product. Pwt-DLR was created by a similar strategy, but using the primer pair GAACTC-GAGTACCTAGATATAAAGAGGAGAAATTAAGCATGG CCTCCAAGGTGTAC GACCCCGAGCAACGCAAACG- CATG SEQ ID NO:17) and GCTAGATCTCCTAGGGGC-CCCCGTCGAGATTTGCTCGTTCTTCAG-CACGCGCTCCACGAAGCTC (SEQ ID NO:18) to amplify the R-luc ORF. Codon 529 variants were created by Quik Change Mutagenesis (Stratagene).

pO-DLR, and its K529 codon variants, were transformed into GeneHog E. coli cells with pSC101*-O-ribosome or pSC101*-ribo-X. pwt-DLR, and its K529 codon variants, were transformed into GeneHog cells with pSC101*-BD. Individual colonies were incubated (37° C., 250 r.p.m., 20 h) in 2 mL LB supplemented with ampicillin (100 µg ml$^{-1}$) and kanamycin (50 µg ml$^{-1}$), pelleted (5000 g, 5 min) and resuspended in 200 µL (1 mg ml$^{-1}$ lysozyme, 10 mM Tris (pH 8.0), 1 mM EDTA). Cells were incubated on ice for 20 min, frozen on dry ice, and thawed on ice. 10 µL samples of this extract were assayed for firefly (F-luc) and Renilla (R-luc) luciferase activity using the Dual-Luciferase Reporter Assay System (Promega). Each ribosome reporter combination was assayed from four independent cultures using an Orion microplate luminometer (Berthold Detection Systems) and the data analyzed as previously described. The error reported is the standard deviation.

Mass Spectrometry

25 µM GST-2BPA-MBP (GST-MBP with Bpas incorporated in response to two amber codons) in 22 µl 40 mM $(NH_4)HCO_3$ was alkylated and digested with chymotrypsin overnight. To obtain a fragment series for the N-terminal Bpa incorporation, 5 µl of a tenfold dilution of the chymotryptic peptide mixture was desalted and concentrated by using a GELoader tip filled with Poros R3 sorbent (Perseptive Biosystems). The bound peptides were eluted with 1 µl of 40% acetonitrile/4% formic acid directly into a nanospray capillary and then introduced into an API QSTAR pulsar i hybrid quadrupole-time-of-flight mass spectrometer (MDS Sciex). Product ion scans were carried out in positive ion-mode and MS survey scans for peptides measured. Selected ions (m/z=668.4$^{4+}$) were fragmented by collision-induced dissociation (CID) with nitrogen in the collision cell and spectra of fragment ions produced were recorded in the time-of-flight mass analyzer. To obtain a fragment series for the C-terminal Bpa incorporation, peptides from the chymotryptic digest were separated by nanoscale liquid chromatography (LC Packings, Amsterdam, The Netherlands) on a reverse-phase C18 column (150×0.075 mm internal diameter, flow rate 0.25 ml min$^{-1}$). The eluate was introduced directly into a Q-STAR hybrid tandem mass spectrometer (LC-MS/MS) and peptide with m/z=469.7$^{4+}$ fragmented.

Protein total mass was determined on an LCT time-of-flight mass spectrometer with electrospray ionization (ESI). (Micromass). Proteins were re-buffered to 10 mM ammonium bicarbonate pH 7.5 and diluted 1:100 into 50% methanol, 1% formic acid. Samples were infused into the ESI source at 10 ml min$^{-1}$, using a Harvard Model 22 infusion pump (Harvard Apparatus) and calibration performed in positive ion mode using horse heart myoglobin. 60-80 scans were acquired and added to yield the mass spectra. Molecular masses were obtained by deconvoluting multiply charged protein mass spectra using MassLynx™ version 4.1 (Micromass). Theoretical molecular masses of wild type proteins were calculated using Protpram, and theoretical masses for unnatural amino acid containing proteins adjusted manually.

REFERENCES TO EXAMPLE 3

1. Xie, J. & Schultz, P. G. A chemical toolkit for proteins—an expanded genetic code. Nat Rev Mol Cell Biol 7, 775-782 (2006).
2. Furter, R. Expansion of the genetic code: site-directed p-fluoro-phenylalanine incorporation in Escherichia coli. Protein Sci 7, 419-426 (1998).
3. Wang, L., Brock, A., Herberich, B. & Schultz, P. G. Expanding the genetic code of Escherichia coli. Science 292, 498-500 (2001).
4. Sakamoto, K. et al. Site-specific incorporation of an unnatural amino acid into proteins in mammalian cells. Nucleic Acids Res 30, 4692-4699 (2002).
5. Chin, J. W. et al. An expanded eukaryotic genetic code. Science 301, 964-967 (2003).
6. Kohrer, C., Xie, L., Kellerer, S., Varshney, U. & RajBhandary, U. L. Import of amber and ochre suppressor tRNAs into mammalian cells: a general approach to site-specific insertion of amino acid analogues into proteins. Proc Natl Acad Sci USA 98, 14310-14315 (2001).
7. Kohrer, C., Yoo, J. H., Bennett, M., Schaack, J. & RajBhandary, U. L. A possible approach to site-specific insertion of two different unnatural amino acids into proteins in mammalian cells via nonsense suppression. Chem Biol 10, 1095-1102 (2003).
8. Lummis, S. C. et al. Cis-trans isomerization at a proline opens the pore of a neurotransmitter-gated ion channel. Nature 438, 248-252 (2005).
9. Nowak, M. W. et al. In vivo incorporation of unnatural amino acids into ion channels in Xenopus oocyte expression system. Methods Enzymol 293, 504-529 (1998).
10. Noren, C. J., Anthony-Cahill, S. J., Griffith, M. C. & Schultz, P. G. A general method for site-specific incorporation of unnatural amino acids into proteins. Science 244, 182-188 (1989).
11. Bain, J. D., Glabe, C. G., Dix, T. A., Chamerlin, A. R. & Diala, E. S. Biosynthetic site-specific incorporation of non-natural amino acids into a polypeptide. J. Am. Chem. Soc 111, 8013-8014 (1989).
12. Heckler, T. G. et al. T4 RNA ligase mediated preparation of novel "chemically misacylated" tRNAPheS. Biochemisty 23, 1468-1473 (1984).
13. Hohsaka, T., Ashizuka, Y., Murakami, H. & Sisido, M. Incorporation of Non-natural amino acids into streptavidin through in vitro frame shift suppression. J. Am. Chem. Soc. 118, 9778-9779 (1996).
14. Murakami, H., Ohta, A., Goto, Y., Sako, Y. & Suga, H. Flexizyme as a versatile tRNA acylation catalyst and the application for translation. Nucleic Acids Symp Ser (Oxf), 35-36 (2006).
15. Capecchi, M. R. Polypeptide chain termination in vitro: isolation of a release factor. Proc Natl Acad Sci USA 58, 1144-1151 (1967).
16. Caskey, C. T., Tompkins, R., Scolnick, E., Caryk, T. & Nirenberg, M. Sequential translation of trinucleotide codons for the initiation and termination of protein synthesis. Science 162, 135-138 (1968).
17. Scolnick, E., Tompkins, R., Caskey, T. & Nirenberg, M. Release factors differing in specificity for terminator codons. Proc Natl Acad Sci USA 61, 768-774 (1968).
18. Dougherty, D. A. Unnatural amino acids as probes of protein structure and function. Curr Opin Chem Biol 4, 645-652 (2000).
19. Mori, H. & Ito, K. Different modes of SecY-SecA interactions revealed by site-directed in vivo photo-cross-linking. Proc Natl Acad Sci USA (2006).
20. Chin, J. W. & Schultz, P. G. In vivo photocrosslinking with unnatural amino Acid mutagenesis. Chembiochem 3, 1135-1137 (2002).
21. Short, G. F., 3rd, Golovine, S. Y. & Hecht, S. M. Effects of release factor 1 on in vitro protein translation and the elaboration of proteins containing unnatural amino acids. *Biochemistry* 38, 8808-8819 (1999).
22. Kleina, L. G., Masson, J. M., Normanly, J., Abelson, J. & Miller, J. H. Construction of *Escherichia coli* amber suppressor tRNA genes. II. Synthesis of additional tRNA genes and improvement of suppressor efficiency. *J Mol Biol* 213, 705-717 (1990).
23. Ryu, Y. & Schultz, P. G. Efficient incorporation of unnatural amino acids into proteins in *Escherichia coli. Nat Methods* 3, 263-265 (2006).
24. Blattner, F. R. et al. The complete genome sequence of *Escherichia coli* K-12. *Science* 277, 1453-1474 (1997).
25. Rackham, O. & Chin, J. W. A network of orthogonal ribosome•mRNA pairs. *Nat Chem Biol* 1, 159-166 (2005).
26. Hui, A. & de Boer, H. A. Specialized ribosome system: preferential translation of a single mRNA species by a subpopulation of mutated ribosomes in *Escherichia coli. Proc Natl Acad Sci USA* 84, 4762-4766 (1987).
27. Triman, K. L., Peister, A. & Goel, R. A. Expanded versions of the 16S and 23S ribosomal RNA mutation databases (16SMDBexp and 23SMDBexp). *Nucleic Acids Res* 26, 280-284 (1998).
28. Schuwirth, B. S. et al. Structures of the bacterial ribosome at 3.5 Å resolution. *Science* 310, 827-834 (2005).
29. Korostelev, A., Trakhanov, S., Laurberg, M. & Noller, H. F. Crystal structure of a 70S ribosome-tRNA complex reveals functional interactions and rearrangements. *Cell* 126, 1065-1077 (2006).
30. Selmer, M. et al. Structure of the 70S ribosome complexed with mRNA and tRNA. *Science* 313, 1935-1942 (2006).
31. Carter, A. P. et al. Functional insights from the structure of the 30S ribosomal subunit and its interactions with antibiotics. *Nature* 407, 340-348 (2000).
32. Petry, S. et al. Crystal structures of the ribosome in complex with release factors RF1 and RF2 bound to a cognate stop codon. *Cell* 123, 1255-1266 (2005).
33. Magliery, T. J., Anderson, J. C. & Schultz, P. G. Expanding the genetic code: selection of efficient suppressors of four-base codons and identification of "shifty" four-base codons with a library approach in *Escherichia coli. J Mol Biol* 307, 755-769 (2001).
34. Cannone, J. J. et al. The comparative RNA web (CRW) site: an online database of comparative sequence and structure information for ribosomal, intron, and other RNAs. *BMC Bioinformatics* 3, 2 (2002).
35. Datta, K. & Majumdar, M. K. A method for assay of chloramphenicol acetyltransferase from crude cell extract. *Microbiologica* 8, 73-77 (1985).
36. Rice, J. B., Libby, R. T. & Reeve, J. N. Mistranslation of the mRNA encoding bacteriophage T7 0.3 protein. *J Biol Chem* 259, 6505-6510 (1984).
37. Kramer, E. B. & Farabaugh, P. J. The frequency of translational misreading errors in *E. coli* is largely determined by tRNA competition. *Rna* 13, 87-96 (2007).
38. Kauer, J. C., Erickson-Viitanen, S., Wolfe, H. R., Jr. & DeGrado, W. F. p-Benzoyl-L-phenylalanine, a new photoreactive amino acid. Photolabeling of calmodulin with a synthetic calmodulin-binding peptide. *J Biol Chem* 261, 10695-10700 (1986).
39. Chin, J. W., Martin, A. B., King, D. S., Wang, L. & Schultz, P. G. Addition of a photocrosslinking amino acid to the genetic code of *Escherichia coli. Proc Natl Acad Sci USA* 99, 11020-11024 (2002).
40. Hino, N. et al. Protein photo-cross-linking in mammalian cells by site-specific incorporation of a photoreactive amino acid. *Nat Methods* 2, 201-206 (2005).
41. Schlieker, C. et al. Substrate recognition by the AAA+ chaperone ClpB. *Nat Struct Mol Biol* 35-11, 607-615 (2004).
42. Weibezahn, J. et al. Thermotolerance requires refolding of aggregated proteins by substrate translocation through the central pore of ClpB. *Cell* 119, 653-665 (2004).
43. Steer, B. A. & Schimmel, P. Major anticodon-binding region missing from an archaebacterial tRNA synthetase. *J Biol Chem* 274, 35601-35606 (1999).
44. Bossi, L. Context effects: translation of UAG codon by suppressor tRNA is affected by the sequence following UAG in the message. *J Mol Biol* 164, 73-87 (1983).
45. Youngman, E. M., Cochella, L., Brunelle, J. L., He, S. & Green, R. Two Distinct Conformations of the Conserved RNA-rich Decoding Center of the Small Ribosomal Subunit Are Recognized by tRNAs and Release Factors. *Cold Spring Harb Symp Quant Biol* 71, 545-549 (2006).
46. Stadtman, T. C. Selenocysteine. *Annu Rev Biochem* 65, 83-100 (1996).
47. Crick, F. H. Codon—anticodon pairing: the wobble hypothesis. *J Mol Biol* 19, 548-555 (1966).
48. Rackham, O. & Chin, J. W. Cellular logic with orthogonal ribosomes. *J Am Chem Soc* 127, 17584-17585 (2005).
49. Murray, I. A. & Shaw, W. V. O-Acetyltransferases for chloramphenicol and other natural products. *Antimicrob Agents Chemother* 41, 1-6 (1997).
50. Lutz, R. & Bujard, H. Independent and tight regulation of transcriptional units in *Escherichia coli* via the LacR/O, the TetR/O and AraC/I1-I2 regulatory elements. *Nucleic Acids Res* 25, 1203-1210 (1997).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

REFERENCES

1. Crick, F. H., Barnett, L., Brenner, S. & Watts-Tobin, R. J. General nature of the genetic code for proteins. *Nature* 192, 1227-1232 (1961).
2. Atkins, J. F. et al. Overriding standard decoding: implications of recoding for ribosome function and enrichment of gene expression. *Cold Spring Harb Symnp Quant Biol* 66, 217-232 (2001).
3. Gesteland, R. F. & Atkins, J. F. Recoding: dynamic reprogramming of translation. *Annu Rev Biochemn* 65, 741-768 (1996).
4. Riyasaty, S. & Atkins, J. F. External suppression of a frameshift mutant in *salmonella. J Mol Biol* 34, 541-557 (1968).
5. Riddle, D. L. & Carbon, J. Frameshift suppression: a nucleotide addition in the anticodon of a glycine transfer RNA. *Nat New Biol* 242, 230-234 (1973).
6. Atkins, J. F., Weiss, R. B., Thompson, S. & Gesteland, R. F. Towards a genetic dissection of the basis of triplet decoding, and its natural subversion: programmed reading frame shifts and hops. *Annu Rev Genet* 25, 201-228 (1991).
7. Anderson, J. C., Magliery, T. J. & Schultz, P. G. Exploring the limits of codon and anticodon size. *Chem Biol* 9, 237-244 (2002).
8. Magliery, T. J., Anderson, J. C. & Schultz, P. G. Expanding the genetic code: selection of efficient suppressors of four-base codons and identification of "shifty" four-base codons with a library approach in *Escherichia coli*. *J Mol Biol* 307, 755-769 (2001).
9. Tuohy, T. M., Thompson, S., Gesteland, R. F. & Atkins, J. F. Seven, eight and nine-membered anticodon loop mutants of tRNA(2Arg) which cause +1 frameshifting. Tolerance of DHU arm and other secondary mutations. *J Mol Biol* 228, 1042-1054 (1992).
10. Taira, H., Fukushima, M., Hohsaka, T. & Sisido, M. Four-base codon-mediated incorporation of non-natural amino acids into proteins in a eukaryotic cell-free translation system. *J Biosci Bioeng* 99, 473-476 (2005).
11. Sisido, M., Ninomiya, K., Ohtsuki, T. & Hohsaka, T. Four-base codon/anticodon strategy and non-enzymatic aminoacylation for protein engineering with non-natural amino acids. *Methods* 36, 270-278 (2005).
12. Taki, M., Matsushita, J. & Sisido, M. Expanding the genetic code in a mammalian cell line by the introduction of four-base codon/anticodon pairs. *Chembiochem* 7, 425-428 (2006).
13. Ohtsuki, T., Manabe, T. & Sisido, M. Multiple incorporation of non-natural amino acids into a single protein using tRNAs with non-standard structures. *FEBS Lett* 579, 6769-6774 (2005).
14. Anderson, J. C. et al. An expanded genetic code with a functional quadruplet codon. *Proc Natl Acad Sci USA* 101, 7566-7571 (2004).
15. Rodriguez, E. A., Lester, H. A. & Dougherty, D. A. In vivo incorporation of multiple unnatural amino acids through nonsense and frameshift suppression. *Proc Natl Acad Sci USA* 103, 8650-8655 (2006).
16. Curran, J. F. & Yarus, M. Reading frame selection and transfer RNA anticodon loop stacking. *Science* 238, 1545-1550 (1987).
17. Stahl, G., McCarty, G. P. & Farabaugh, P. J. Ribosome structure: revisiting the connection between translational accuracy and unconventional decoding. *Trends Biochem Sci* 27, 178-183 (2002).
18. Roth, J. R. Frameshift suppression. *Cell* 24, 601-602 (1981).
19. Bossi, L. & Roth, J. R. Four-base codons ACCA, ACCU and ACCC are recognized by frameshift suppressor sufJ. *Cell* 25, 489-496 (1981).
20. Ramakrishnan, V. Ribosome structure and the mechanism of translation. *Cell* 108, 557-572 (2002).
21. Triman, K. L., Peister, A. & Goel, R. A. Expanded versions of the 16S and 23S ribosomal RNA mutation databases (16SMDBexp and 23SMDBexp). *Nucleic Acids Res* 26, 280-284 (1998).
22. Rackham, O. & Chin, J. W. A network of orthogonal ribosome x mRNA pairs. *Nat Chem Biol* 1, 159-166 (2005).
23. Rackham, O. & Chin, J. W. Cellular logic with orthogonal ribosomes. *J Am Chem Soc* 127, 17584-17585 (2005).
24. Rackham, O., Wang, K. & Chin, J. W. Functional epitopes at the ribosome subunit interface. *Nat Chem Biol* 2, 254-258 (2006).
25. Hansen, T. M., Baranov, P. V., Ivanov, I. P., Gesteland, R. F. & Atkins, J. F. Maintenance of the correct open reading frame by the ribosome. *EMBO Rep* 4, 499-504 (2003).
26. Schuwirth, B. S. et al. Structures of the bacterial ribosome at 3.5 Å resolution. *Science* 310, 827-834 (2005).
27. Korostelev, A., Trakhanov, S., Laurberg, M. & Noller, H. F. Crystal structure of a 70S ribosome-tRNA complex reveals functional interactions and rearrangements. *Cell* 126, 1065-1077 (2006).
28. Selmer, M. et al. Structure of the 70S ribosome complexed with mRNA and tRNA. *Science* 313, 1935-1942 (2006).
29. Ogle, J. M., Carter, A. P. & Ramakrishnan, V. Insights into the decoding mechanism from recent ribosome structures. *Trends Biochem Sci* 28, 259-266 (2003).
30. Carter, A. P. et al. Functional insights from the structure of the 30S ribosomal subunit and its interactions with antibiotics. *Nature* 407, 340-348 (2000).
31. Murray, I. A. & Shaw, W. V. O-Acetyltransferases for chloramphenicol and other natural products. *Antimicrob Agents Chemother* 41, 1-6 (1997).
32. Datta, K. & Majumdar, M. K. A method for assay of chloramphenicol acetyltransferase from crude cell extract. *Microbiologica* 8, 73-77 (1985).
33. Moore, B., Nelson, C. C., Persson, B. C., Gesteland, R. F. & Atkins, J. F. Decoding of tandem quadruplets by adjacent tRNAs with eight-base anticodon loops. *Nucleic Acids Res* 28, 3615-3624 (2000).
34. Janzen, D. M. & Geballe, A. P. Modulation of translation termination mechanisms by cis- and trans-acting factors. *Cold Spring Harb Symp Quant Biol* 66, 459-467 (2001).
35. Petry, S. et al. Crystal structures of the ribosome in complex with release factors RF1 and RF2 bound to a cognate stop codon. *Cell* 123, 1255-1266 (2005).
36. Zhang, S., Ryden-Aulin, M., Kirsebom, L. A. & Isaksson, L. A. Genetic implication for an interaction between release factor one and ribosomal protein L7/L12 in vivo. *J Mol Biol* 242, 614-618 (1994).
37. Prescott, C. D. & Komau, H. C. Mutations in *E. coli* 16s rRNA that enhance and decrease the activity of a suppressor tRNA. *Nucleic Acids Res* 20, 1567-1571 (1992).
38. Arkov, A. L., Freistroffer, D. V., Ehrenberg, M. & Murgola, E. J. Mutations in RNAs of both ribosomal subunits cause defects in translation termination. *Embo J* 17, 1507-1514 (1998).
39. Sprinzl, M., Horn, C., Brown, M., Ioudovitch, A. & Steinberg, S. Compilation of tRNA sequences and sequences of tRNA genes. *Nucleic Acids Res* 26, 148-153 (1998).
40. Olejniczak, M., Dale, T., Fahlman, R. P. & Uhlenbeck, O. C. Idiosyncratic tuning of tRNAs to achieve uniform ribosome binding. *Nat Struct Mol Biol* 12, 788-793 (2005).
41. Link, A. J., Mock, M. L. & Tirrell, D. A. Non-canonical amino acids in protein engineering. *Curr Opin Biotechnol* 14, 603-609 (2003).
42. Chin, J. W. et al. An expanded eukaryotic genetic code. *Science* 301, 964-967 (2003).
43. Nowak, M. W. et al. Nicotinic receptor binding site probed with unnatural amino acid incorporation in intact cells. *Science* 268, 439-442 (1995).
44. Xie, J. & Schultz, P. G. A chemical toolkit for proteins—an expanded genetic code. *Nat Rev Mol Cell Biol* 7, 775-782 (2006).
45. England, P. M., Zhang, Y., Dougherty, D. A. & Lester, H. A. Backbone mutations in transmembrane domains of a ligand-gated ion channel: implications for the mechanism of gating. *Cell* 96, 89-98 (1999).
46. Mori, H. & Ito, K. Different modes of SecY-SecA interactions revealed by site-directed in vivo photo-cross-linking. *Proc Natl Acad Sci USA* (2006).
47. Crick, F. H. Codon—anticodon pairing: the wobble hypothesis. *J Mol Biol* 19, 548-555 (1966).
48. Adleman, L. M. Molecular computation of solutions to combinatorial problems. *Science* 266, 1021-1024 (1994).
49. Benenson, Y. et al. Programmable and autonomous computing machine made of biomolecules. *Nature* 414, 430-434 (2001)

The invention claimed is:

1. An evolved orthogonal ribosomal RNA (rRNA) which possesses an enhanced efficiency of tRNA-dependent reading of orthogonal mRNA codons, wherein said orthogonal rRNA is a 16S rRNA containing a mutated 530 loop such that the 16S rRNA comprises the sequence 529-GGGAAAA-535.

2. An evolved orthogonal rRNA according to claim 1, wherein the orthogonal mRNA codons are extended codons or stop codons.

3. An evolved orthogonal rRNA according to claim 2, wherein the orthogonal mRNA codon is a quadruplet codon or an amber stop codon.

4. An evolved orthogonal rRNA according to claim 1, which possesses a decreased functional interaction with release factor 1 (RF-1).

5. An orthogonal ribosome incorporating an evolved orthogonal rRNA according to claim 1.

6. A cell comprising two or more protein translation mechanisms, wherein:

(a) a first mechanism is the natural translation mechanism wherein mRNA is translated by a ribosome in accordance with the natural genetic code; and (b) a second mechanism is an artificial mechanism, in which orthogonal mRNA comprising orthogonal codons is translated by an orthogonal ribosome;

wherein the orthogonal codons in the orthogonal mRNA are (i) not translated by the natural ribosome, or (ii) translated more efficiently by the orthogonal ribosome than by the natural ribosome, or (iii) translated into different polypeptides by the orthogonal ribosome and the natural ribosome, and wherein the orthogonal ribosome incorporates an evolved orthogonal ribosomal RNA (rRNA) which possesses an enhanced efficiency of tRNA-dependent reading of orthogonal mRNA codons, wherein said orthogonal rRNA is a 16S rRNA containing a mutated 530 loop such that the 16S rRNA comprises the sequence 529-GG-GAAAA-535.

* * * * *

UNITED STATES PATENT AND TRADEMARK OFFICE
CERTIFICATE OF CORRECTION

| | | |
|---|---|---|
| PATENT NO. | : 8,497,231 B2 | Page 1 of 1 |
| APPLICATION NO. | : 12/516230 | |
| DATED | : July 30, 2013 | |
| INVENTOR(S) | : Chin et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 290 days.

Signed and Sealed this
Tenth Day of February, 2015

Michelle K. Lee
*Deputy Director of the United States Patent and Trademark Office*

SEQUENCE LISTING

```
<160> NUMBER OF SEQ ID NOS: 68

<210> SEQ ID NO 1
<211> LENGTH: 65
<212> TYPE: DNA
<213> ORGANISM: Artificial Sequence
<220> FEATURE:
<223> OTHER INFORMATION: primer

<400> SEQUENCE: 1
gaactcgaga caattttcat atccctccgc aaatgtcccc tatactaggt tattggaaaa    60
ttaag                                                                65

<210> SEQ ID NO 2
<211> LENGTH: 45
<212> TYPE: DNA
<213> ORGANISM: Artificial Sequence
<220> FEATURE:
<223> OTHER INFORMATION: primer

<400> SEQUENCE: 2
gaagaggtac ccgtcacgat gaattcccgg ggatccacgc ggaac                    45

<210> SEQ ID NO 3
<211> LENGTH: 39
<212> TYPE: DNA
<213> ORGANISM: Artificial Sequence
<220> FEATURE:
<223> OTHER INFORMATION: PRIMER/RNA

<400> SEQUENCE: 3
gaagggtacc tcaaaatcga agaaggtaaa ctggtaatc                           39

<210> SEQ ID NO 4
<211> LENGTH: 30
<212> TYPE: DNA
<213> ORGANISM: Artificial Sequence
<220> FEATURE:
<223> OTHER INFORMATION: PRIMER/RNA

<400> SEQUENCE: 4
ccaaagctta gcttgcctgc aggtcgactc                                     30

<210> SEQ ID NO 5
<211> LENGTH: 72
<212> TYPE: DNA
<213> ORGANISM: Artificial Sequence
<220> FEATURE:
<223> OTHER INFORMATION: PRIMER/RNA

<400> SEQUENCE: 5
gtaggtctcg gatccccggg tacctagaat taaagaggag aaattaagca tgtcccctat    60
actaggttat tg                                                        72

<210> SEQ ID NO 6
<211> LENGTH: 76
<212> TYPE: DNA
<213> ORGANISM: Artificial Sequence
<220> FEATURE:
<223> OTHER INFORMATION: PRIMER/RNA

<400> SEQUENCE: 6
gtaggtctcg gatcctctag agtcgacctg caggaatgca agcttggcgt aactcgagcc    60
```
gctcacaatt ccacac                                                        76

<210> SEQ ID NO 7
<211> LENGTH: 52
<212> TYPE: DNA
<213> ORGANISM: Artificial Sequence
<220> FEATURE:
<223> OTHER INFORMATION: PRIMER/RNA

<400> SEQUENCE: 7
gaattcatcg tgacgggtag ctcaaaatcg aagaaggtaa actggtaatc tg               52

<210> SEQ ID NO 8
<211> LENGTH: 52
<212> TYPE: DNA
<213> ORGANISM: Artificial Sequence
<220> FEATURE:
<223> OTHER INFORMATION: PRIMER/RNA

<400> SEQUENCE: 8
cttcgatttt gagctacccg tcacgatgaa ttcccgggga tccacgcgga ac               52

<210> SEQ ID NO 9
<211> LENGTH: 49
<212> TYPE: DNA
<213> ORGANISM: Artificial
<220> FEATURE:
<223> OTHER INFORMATION: PRIMER/RNA

<400> SEQUENCE: 9
ctcaaaatct aggaaggtaa actggtaatc tggattaacg gcgataaag                   49

<210> SEQ ID NO 10
<211> LENGTH: 39
<212> TYPE: DNA
<213> ORGANISM: Artificial Sequence
<220> FEATURE:
<223> OTHER INFORMATION: PRIMER/RNA

<400> SEQUENCE: 10
cagtttacct tcctagattt tgagctaccc gtcacgatg                              39

<210> SEQ ID NO 11
<211> LENGTH: 31
<212> TYPE: DNA
<213> ORGANISM: Artificial Sequence
<220> FEATURE:
<223> OTHER INFORMATION: PRIMER/RNA

<400> SEQUENCE: 11
actggatcct gctagaggca tcaaataaaa c                                      31

<210> SEQ ID NO 12
<211> LENGTH: 29
<212> TYPE: DNA
<213> ORGANISM: Artificial Sequence
<220> FEATURE:
<223> OTHER INFORMATION: PRIMER/RNA

<400> SEQUENCE: 12
agtaccggtt agacgtcgga attgccagc                                         29

<210> SEQ ID NO 13
<211> LENGTH: 77
<212> TYPE: DNA
<213> ORGANISM: Artificial Sequence
<220> FEATURE:

```
-continued

<223> OTHER INFORMATION: PRIMER/RNA

<400> SEQUENCE: 13
gaactcgagg gcgcggcttt catatccctc cgcaaatggc ctccaaggtg tacgaccccg    60
agcaacgcaa acgcatg                                                  77

<210> SEQ ID NO 14
<211> LENGTH: 64
<212> TYPE: DNA
<213> ORGANISM: Artificial Sequence
<220> FEATURE:
<223> OTHER INFORMATION: PRIMER/RNA

<400> SEQUENCE: 14
gctagatctc ctaggggccc ccgtcgagat ttgctcgttc ttcagcacgc gctccacgaa    60
gctc                                                                64

<210> SEQ ID NO 15
<211> LENGTH: 67
<212> TYPE: DNA
<213> ORGANISM: Artificial Sequence
<220> FEATURE:
<223> OTHER INFORMATION: PRIMER/RNA

<400> SEQUENCE: 15
aggagatcta gcgctggatc ccccggggag ctcatcgaag atgccaaaaa cattaagaag    60
ggcccag                                                             67

<210> SEQ ID NO 16
<211> LENGTH: 35
<212> TYPE: DNA
<213> ORGANISM: Artificial Sequence
<220> FEATURE:
<223> OTHER INFORMATION: PRIMER/RNA

<400> SEQUENCE: 16
gacaagctta cacggcgatc ttgccgccct tcttg                              35

<210> SEQ ID NO 17
<211> LENGTH: 80
<212> TYPE: DNA
<213> ORGANISM: Artificial Sequence
<220> FEATURE:
<223> OTHER INFORMATION: PRIMER/RNA

<400> SEQUENCE: 17
gaactcgagt acctagatat aaagaggaga aattaagcat ggcctccaag gtgtacgacc    60
ccgagcaacg caaacgcatg                                               80

<210> SEQ ID NO 18
<211> LENGTH: 64
<212> TYPE: DNA
<213> ORGANISM: Artificial Sequence
<220> FEATURE:
<223> OTHER INFORMATION: PRIMER/RNA

<400> SEQUENCE: 18
gctagatctc ctaggggccc ccgtcgagat ttgctcgttc ttcagcacgc gctccacgaa    60
gctc                                                                64

<210> SEQ ID NO 19
<211> LENGTH: 21
<212> TYPE: RNA
```

```
<213> ORGANISM: Artificial Sequence
<220> FEATURE:
<223> OTHER INFORMATION: Synthesized

<400> SEQUENCE: 19
agcagccgcg guaauacgga g                                              21

<210> SEQ ID NO 20
<211> LENGTH: 21
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<222> LOCATION: (10)..(16)
<223> OTHER INFORMATION: n is a, c, g, or u

<400> SEQUENCE: 20
agcagccgcn nnnnncgga g                                               21

<210> SEQ ID NO 21
<211> LENGTH: 19
<212> TYPE: RNA
<213> ORGANISM: Artificial
<220> FEATURE:
<223> OTHER INFORMATION: Synthesized
<220> FEATURE:
<221> NAME/KEY: misc_feature
<222> LOCATION: (10)..(14)
<223> OTHER INFORMATION: n is a, c, g, or u

<400> SEQUENCE: 21
agcagccgcn nnnncggag                                                 19

<210> SEQ ID NO 22
<211> LENGTH: 20
<212> TYPE: RNA
<213> ORGANISM: Artificial Sequence
<220> FEATURE:
<223> OTHER INFORMATION: RNA
<220> FEATURE:
<221> NAME/KEY: misc_feature
<222> LOCATION: (10)..(15)
<223> OTHER INFORMATION: n is a, c, g, or u

<400> SEQUENCE: 22
agcagccgcn nnnnncggag                                                20

<210> SEQ ID NO 23
<211> LENGTH: 22
<212> TYPE: RNA
<213> ORGANISM: Artificial
<220> FEATURE:
<223> OTHER INFORMATION: Synthesized
<220> FEATURE:
<221> NAME/KEY: misc_feature
<222> LOCATION: (10)..(17)
<223> OTHER INFORMATION: n is a, c, g, or u

<400> SEQUENCE: 23
agcagccgcn nnnnnncgg ag                                              22

<210> SEQ ID NO 24
<211> LENGTH: 23
<212> TYPE: RNA
<213> ORGANISM: Artificial Sequence
<220> FEATURE:
<223> OTHER INFORMATION: Synthesized
<220> FEATURE:
```

```
<221> NAME/KEY: misc_feature
<222> LOCATION: (10)..(18)
<223> OTHER INFORMATION: n is a, c, g, or u

<400> SEQUENCE: 24
agcagccgcn nnnnnnncg gag                                              23

<210> SEQ ID NO 25
<211> LENGTH: 15
<212> TYPE: DNA
<213> ORGANISM: Artificial
<220> FEATURE:
<223> OTHER INFORMATION: Synthesized

<400> SEQUENCE: 25
acgttttcat cgctc                                                      15

<210> SEQ ID NO 26
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(10)
<223> OTHER INFORMATION: n is a, c, g, t or u

<400> SEQUENCE: 26
acgtttnnnn tcgctc                                                     16

<210> SEQ ID NO 27
<211> LENGTH: 15
<212> TYPE: DNA
<213> ORGANISM: Artificial
<220> FEATURE:
<223> OTHER INFORMATION: Synthesized

<400> SEQUENCE: 27
acgttttaga gtctc                                                      15

<210> SEQ ID NO 28
<211> LENGTH: 15
<212> TYPE: DNA
<213> ORGANISM: Artificial Sequence
<220> FEATURE:
<223> OTHER INFORMATION: Synthesized

<400> SEQUENCE: 28
ttcgtctcag ccaat                                                      15

<210> SEQ ID NO 29
<211> LENGTH: 16
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(10)
<223> OTHER INFORMATION: n is a, c, g, t or u

<400> SEQUENCE: 29
ttcgtcnnnn gccaat                                                     16

<210> SEQ ID NO 30
<211> LENGTH: 5
<212> TYPE: PRT
```

```
<213> ORGANISM: Artificial Sequence
<220> FEATURE:
<223> OTHER INFORMATION: Synthesized

<400> SEQUENCE: 30

Thr Phe Ser Ser Leu
1               5

<210> SEQ ID NO 31
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 31

Thr Phe Xaa Ser Leu
1               5

<210> SEQ ID NO 32
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 32

Thr Phe Xaa Ser Leu
1               5

<210> SEQ ID NO 33
<211> LENGTH: 5
<212> TYPE: PRT
<213> ORGANISM: Artificial Sequence
<220> FEATURE:
<223> OTHER INFORMATION: Synthesized

<400> SEQUENCE: 33

Phe Val Ser Ala Asn
1               5

<210> SEQ ID NO 34
<211> LENGTH: 5
<212> TYPE: PRT
<213> ORGANISM: Artificial Sequence
<220> FEATURE:
<223> OTHER INFORMATION: Synthesized
<220> FEATURE:
<221> NAME/KEY: misc_feature
<222> LOCATION: (3)..(3)
<223> OTHER INFORMATION: Xaa can be any naturally occurring amino acid

<400> SEQUENCE: 34

Phe Val Xaa Ala Asn
1               5

<210> SEQ ID NO 35
<211> LENGTH: 54
<212> TYPE: DNA
<213> ORGANISM: Artificial Sequence
<220> FEATURE:
<223> OTHER INFORMATION: Synthesized
```

<220> FEATURE:
<221> NAME/KEY: misc_feature
<222> LOCATION: (21)..(25)
<223> OTHER INFORMATION: n is a, c, g, or t

<400> SEQUENCE: 35
ggaaaggtct cagcagccgc nnnnncggag ggtgcaagcg ttaatcggaa ttac         54

<210> SEQ ID NO 36
<211> LENGTH: 55
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(26)
<223> OTHER INFORMATION: n is a, c, g, or t

<400> SEQUENCE: 36
ggaaaggtct cagcagccgc nnnnnncgga gggtgcaagc gttaatcgga attac         55

<210> SEQ ID NO 37
<211> LENGTH: 56
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(27)
<223> OTHER INFORMATION: n is a, c, g, or t

<400> SEQUENCE: 37
ggaaaggtct cagcagccgc nnnnnnncgg agggtgcaag cgttaatcgg aattac         56

<210> SEQ ID NO 38
<211> LENGTH: 57
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(28)
<223> OTHER INFORMATION: n is a, c, g, or t

<400> SEQUENCE: 38
ggaaaggtct cagcagccgc nnnnnnnncg gagggtgcaa gcgttaatcg gaattac         57

<210> SEQ ID NO 39
<211> LENGTH: 58
<212> TYPE: DNA
<213> ORGANISM: Artificial Sequence
<220> FEATURE:
<223> OTHER INFORMATION: Synthesized
<220> FEATURE:
<221> NAME/KEY: misc_feature
<222> LOCATION: (21)..(29)
<223> OTHER INFORMATION: n is a, c, g, or t

<400> SEQUENCE: 39
ggaaaggtct cagcagccgc nnnnnnnnnc ggagggtgca agcgttaatc ggaattac         58

<210> SEQ ID NO 40
<211> LENGTH: 45
<212> TYPE: DNA
<213> ORGANISM: Artificial Sequence
<220> FEATURE:
<223> OTHER INFORMATION: Synthesized

<400> SEQUENCE: 40
gagtaggtct cactgctggc acggagttag ccggtgcttc ttctg        45

<210> SEQ ID NO 41
<211> LENGTH: 96
<212> TYPE: DNA
<213> ORGANISM: Artificial
<220> FEATURE:
<223> OTHER INFORMATION: Synthesized

<400> SEQUENCE: 41
cacaagtata cgccgcttct ttgagcgaac gatcaaaaat aagtggcgcc ccatcaaaaa        60
aatattctca acataaaaaa ctttgtgtaa tacttg        96

<210> SEQ ID NO 42
<211> LENGTH: 88
<212> TYPE: DNA
<213> ORGANISM: Artificial Sequence
<220> FEATURE:
<223> OTHER INFORMATION: Synthesized

<400> SEQUENCE: 42
ctcaacataa aaactttgt gtaatacttg taacgctgaa ttcacgtggc cggccatatg        60
ggagagatgc cggagcggct gaacggac        88

<210> SEQ ID NO 43
<211> LENGTH: 91
<212> TYPE: DNA
<213> ORGANISM: Artificial Sequence
<220> FEATURE:
<223> OTHER INFORMATION: Synthesized

<400> SEQUENCE: 43
gtggcggaga gaggggatt tgaaccccg gtagagttgc ccctactccg gtgttagaat        60
accggtccgt tcagccgctc cggcatctct c        91

<210> SEQ ID NO 44
<211> LENGTH: 88
<212> TYPE: DNA
<213> ORGANISM: Artificial Sequence
<220> FEATURE:
<223> OTHER INFORMATION: Synthesized

<400> SEQUENCE: 44
cacaagtata cttaaaaaaa atccttagct ttcgctaagg atctgcagcc cgggcgcgcc        60
taggtggcgg agagagggg atttgaac        88

<210> SEQ ID NO 45
<211> LENGTH: 50
<212> TYPE: DNA
<213> ORGANISM: Artificial Sequence
<220> FEATURE:
<223> OTHER INFORMATION: Synthesized

<400> SEQUENCE: 45
cagactgaaa cgttttagat cgctctggag tgaataccac gacgatttcc        50

<210> SEQ ID NO 46
<211> LENGTH: 50
<212> TYPE: DNA
<213> ORGANISM: Artificial Sequence
<220> FEATURE:
<223> OTHER INFORMATION: Synthesized

```
<400> SEQUENCE: 46
ttcactccag agcgatctaa aacgtttcag tctgctcatg gaaaacggtg              50

<210> SEQ ID NO 47
<211> LENGTH: 50
<212> TYPE: DNA
<213> ORGANISM: Artificial Sequence
<220> FEATURE:
<223> OTHER INFORMATION: Synthesized

<400> SEQUENCE: 47
aatatgtttt tcgtctagag ccaatccctg ggtgagtttc accagttttg              50

<210> SEQ ID NO 48
<211> LENGTH: 51
<212> TYPE: DNA
<213> ORGANISM: Artificial Sequence
<220> FEATURE:
<223> OTHER INFORMATION: Synthesized

<400> SEQUENCE: 48
cacccaggga ttggctctag acgaaaaaca tattctcaat aaacccttta g            51

<210> SEQ ID NO 49
<211> LENGTH: 49
<212> TYPE: DNA
<213> ORGANISM: Artificial
<220> FEATURE:
<223> OTHER INFORMATION: Synthesized

<400> SEQUENCE: 49
cagactgaaa cgttttagtc gctctggagt gaataccacg acgatttcc               49

<210> SEQ ID NO 50
<211> LENGTH: 49
<212> TYPE: DNA
<213> ORGANISM: Artificial Sequence
<220> FEATURE:
<223> OTHER INFORMATION: Synthesized

<400> SEQUENCE: 50
ttcactccag agcgactaaa acgtttcagt ctgctcatgg aaaacggtg               49

<210> SEQ ID NO 51
<211> LENGTH: 49
<212> TYPE: DNA
<213> ORGANISM: Artificial Sequence
<220> FEATURE:
<223> OTHER INFORMATION: Synthesized

<400> SEQUENCE: 51
aatatgtttt tcgtctaggc caatccctgg gtgagtttca ccagttttg               49

<210> SEQ ID NO 52
<211> LENGTH: 50
<212> TYPE: DNA
<213> ORGANISM: Artificial Sequence
<220> FEATURE:
<223> OTHER INFORMATION: Synthesized

<400> SEQUENCE: 52
cacccaggga ttggcctaga cgaaaaacat attctcaata aacccttag               50

<210> SEQ ID NO 53
<211> LENGTH: 50
```

```
<212> TYPE: DNA
<213> ORGANISM: Artificial Sequence
<220> FEATURE:
<223> OTHER INFORMATION: Synthesized

<400> SEQUENCE: 53
ctactccggt gttagtatac cggtccgttc agccgctccg gcatctctcc          50

<210> SEQ ID NO 54
<211> LENGTH: 50
<212> TYPE: DNA
<213> ORGANISM: Artificial Sequence
<220> FEATURE:
<223> OTHER INFORMATION: Synthesized

<400> SEQUENCE: 54
tgaacggacc ggtatactaa caccggagta ggggcaactc taccgggggt          50

<210> SEQ ID NO 55
<211> LENGTH: 15
<212> TYPE: DNA
<213> ORGANISM: Artificial Sequence
<220> FEATURE:
<223> OTHER INFORMATION: Synthesized

<400> SEQUENCE: 55
acgttttcat cgctc                                               15

<210> SEQ ID NO 56
<211> LENGTH: 16
<212> TYPE: DNA
<213> ORGANISM: Artificial Sequence
<220> FEATURE:
<223> OTHER INFORMATION: Synthesized

<400> SEQUENCE: 56
acgtttuaga tcgctc                                              16

<210> SEQ ID NO 57
<211> LENGTH: 15
<212> TYPE: DNA
<213> ORGANISM: Artificial Sequence
<220> FEATURE:
<223> OTHER INFORMATION: Synthesized

<400> SEQUENCE: 57
ttcgtctcag ccaat                                               15

<210> SEQ ID NO 58
<211> LENGTH: 16
<212> TYPE: DNA
<213> ORGANISM: Artificial Sequence
<220> FEATURE:
<223> OTHER INFORMATION: Synthesized

<400> SEQUENCE: 58
ttcgtcuaga gccaat                                              16

<210> SEQ ID NO 59
<211> LENGTH: 72
<212> TYPE: DNA
<213> ORGANISM: Artificial Sequence
<220> FEATURE:
<223> OTHER INFORMATION: Synthesized

<400> SEQUENCE: 59
ctggttccgc gtggatcccc gggaattcat cgtgacgggt acctcaaaat cgaagaaggt  60
```

-continued

```
aaactggtaa tc                                                      72

<210> SEQ ID NO 60
<211> LENGTH: 24
<212> TYPE: PRT
<213> ORGANISM: Artificial Sequence
<220> FEATURE:
<223> OTHER INFORMATION: Synthesized

<400> SEQUENCE: 60

Leu Val Pro Arg Gly Ser Pro Gly Ile His Arg Asp Gly Tyr Leu Lys
1               5                   10                  15

Ile Glu Glu Gly Lys Leu Val Ile
            20

<210> SEQ ID NO 61
<211> LENGTH: 17
<212> TYPE: RNA
<213> ORGANISM: Artificial Sequence
<220> FEATURE:
<223> OTHER INFORMATION: Synthesized

<400> SEQUENCE: 61
ccgcggaaau acggagg                                                 17

<210> SEQ ID NO 62
<211> LENGTH: 17
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(11)
<223> OTHER INFORMATION: n is a, c, g, or u

<400> SEQUENCE: 62
ccgcnnnnnn ncggagg                                                 17

<210> SEQ ID NO 63
<211> LENGTH: 17
<212> TYPE: RNA
<213> ORGANISM: Artificial Sequence
<220> FEATURE:
<223> OTHER INFORMATION: Synthesized

<400> SEQUENCE: 63
ccgcgggaaa acggagg                                                 17

<210> SEQ ID NO 64
<211> LENGTH: 17
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<222> LOCATION: (7)..(7)
<223> OTHER INFORMATION: n is a, c, g, or u

<400> SEQUENCE: 64
ccgcggnaaa acggagg                                                 17

<210> SEQ ID NO 65
<211> LENGTH: 17
<212> TYPE: RNA
<213> ORGANISM: Artificial
```

```
<220> FEATURE:
<223> OTHER INFORMATION: Synthesized

<400> SEQUENCE: 65
ccgcgguaau acggagg                                              17

<210> SEQ ID NO 66
<211> LENGTH: 17
<212> TYPE: RNA
<213> ORGANISM: Artificial Sequence
<220> FEATURE:
<223> OTHER INFORMATION: Synthesized
<220> FEATURE:
<221> NAME/KEY: misc_feature
<222> LOCATION: (5)..(11)
<223> OTHER INFORMATION: n is a, c, g, or u

<400> SEQUENCE: 66
ccgcnnnnnn ncggagg                                              17

<210> SEQ ID NO 67
<211> LENGTH: 17
<212> TYPE: RNA
<213> ORGANISM: Artificial Sequence
<220> FEATURE:
<223> OTHER INFORMATION: Synthesized

<400> SEQUENCE: 67
ccgcgggaaa acggagg                                              17

<210> SEQ ID NO 68
<211> LENGTH: 15
<212> TYPE: DNA
<213> ORGANISM: Artificial Sequence
<220> FEATURE:
<223> OTHER INFORMATION: Synthesized

<400> SEQUENCE: 68
acgtttuaga gtctc                                                15
```